US008629119B2

(12) United States Patent
Olson et al.

(10) Patent No.: US 8,629,119 B2
(45) Date of Patent: Jan. 14, 2014

(54) DUAL TARGETING OF MIR-208 AND MIR-499 IN THE TREATMENT OF CARDIAC DISORDERS

(75) Inventors: Eric Olson, Dallas, TX (US); Eva van Rooij, Boulder, CO (US)

(73) Assignee: The Board of Regents, The University of Texas System, Austin, TX (US)

( * ) Notice: Subject to any disclaimer, the term of this patent is extended or adjusted under 35 U.S.C. 154(b) by 31 days.

(21) Appl. No.: 13/147,784

(22) PCT Filed: Feb. 4, 2010

(86) PCT No.: PCT/US2010/023234
§ 371 (c)(1),
(2), (4) Date: Oct. 18, 2011

(87) PCT Pub. No.: WO2010/091204
PCT Pub. Date: Aug. 12, 2010

(65) Prior Publication Data
US 2012/0035243 A1 Feb. 9, 2012

Related U.S. Application Data

(60) Provisional application No. 61/149,915, filed on Feb. 4, 2009.

(51) Int. Cl.
*C12N 15/11* (2006.01)
*C07H 21/04* (2006.01)
(52) U.S. Cl.
USPC ........................................ 514/44 A; 536/24.5
(58) Field of Classification Search
None
See application file for complete search history.

(56) References Cited

U.S. PATENT DOCUMENTS

| 7,232,806 B2 | 6/2007 | Tuschl et al. |
|---|---|---|
| 2004/0157790 A1 | 8/2004 | Herweijer et al. |
| 2005/0059005 A1 | 3/2005 | Tuschl et al. |
| 2005/0075492 A1 | 4/2005 | Chen et al. |
| 2005/0124568 A1 | 6/2005 | Usman et al. |
| 2005/0261218 A1 | 11/2005 | Esau et al. |
| 2006/0019286 A1 | 1/2006 | Horvitz et al. |
| 2006/0185027 A1 | 8/2006 | Bartel et al. |
| 2007/0287179 A1 | 12/2007 | Tuschl et al. |
| 2007/0292878 A1 | 12/2007 | Raymond |
| 2008/0050744 A1 | 2/2008 | Brown et al. |
| 2008/0176766 A1 | 7/2008 | Brown et al. |
| 2008/0214437 A1 | 9/2008 | Mohapatra et al. |
| 2009/0137504 A1 | 5/2009 | Echwald et al. |
| 2009/0143326 A1 | 6/2009 | Obad et al. |
| 2009/0180957 A1 | 7/2009 | Olson et al. |
| 2009/0286969 A1 | 11/2009 | Esau et al. |
| 2009/0291906 A1 | 11/2009 | Esau et al. |
| 2009/0291907 A1 | 11/2009 | Esau et al. |
| 2009/0293148 A1 | 11/2009 | Ren et al. |
| 2009/0317369 A1 | 12/2009 | Hosoda et al. |
| 2009/0326049 A1 | 12/2009 | Aristarkhov et al. |
| 2010/0029003 A1 | 2/2010 | Bartel et al. |
| 2010/0269183 A1 | 10/2010 | Olson et al. |
| 2010/0280094 A1 | 11/2010 | Beuvink et al. |

FOREIGN PATENT DOCUMENTS

| EP | 1777301 A2 | 4/2007 |
|---|---|---|
| EP | 1959012 A2 | 8/2008 |
| EP | 2113567 A1 | 11/2009 |
| JP | 2004-522411 | 7/2004 |
| JP | 2006-502693 | 1/2006 |
| JP | 2006-101790 | 4/2006 |
| WO | WO 02/10453 A2 | 2/2002 |
| WO | WO 03/065993 A2 | 8/2003 |
| WO | WO 2005/013901 A2 | 2/2005 |
| WO | WO 2005/017145 A1 | 2/2005 |
| WO | WO 2005/078096 A2 | 8/2005 |
| WO | WO 2005/078139 A2 | 8/2005 |
| WO | WO 2005/079397 A2 | 9/2005 |
| WO | WO 2005/118806 A2 | 12/2005 |
| WO | WO 2006/013561 A2 | 2/2006 |
| WO | WO 2006/047454 A2 | 5/2006 |
| WO | WO 2006/063356 A1 | 6/2006 |
| WO | WO 2006/111512 A1 | 10/2006 |
| WO | WO 2006/137941 A2 | 12/2006 |
| WO | WO 2007/000668 A2 | 1/2007 |
| WO | WO 2007/035684 A2 | 3/2007 |
| WO | WO 2007/070483 A2 | 6/2007 |
| WO | WO 2007/073737 A1 | 7/2007 |
| WO | WO 2007/090073 A2 | 8/2007 |
| WO | WO 2007/112754 A2 | 10/2007 |
| WO | WO 2008/016924 A2 | 2/2008 |
| WO | WO 2008/042231 A2 | 4/2008 |
| WO | WO 2008/043521 A2 | 4/2008 |
| WO | WO 2008/061537 A2 | 5/2008 |

(Continued)

OTHER PUBLICATIONS

Lagos-Quintana et al., "New microRNAs from mouse and human," RNA, vol. 9:175-179, 2003.
Lagos-Quintana et al., "Identification of tissue-specific microRNAs from mouse," Current Biology, vol. 12:735-739, 2002.
Sempere et al., "Expression profiling of mammalian microRNAs uncovers a subset of brain-expressed microRNAs with possible roles in murine and human neuronal differentiation," Genome Biology, vol. 5:R13, 2004.
Van Rooij et al., "A signature pattern of stress-responsive microRNAs that can evoke cardiac hypertrophy and heart failure," Proc. Natl. Acad. Sci. USA, vol. 103: 18255-18260, 2006.
Landgraf et al., "A mammalian microRNA expression atlas based on small RNA library sequencing," Cell, vol. 129: 1401-1414, 2007.

(Continued)

*Primary Examiner* — Jennifer Pitrak McDonald
(74) *Attorney, Agent, or Firm* — Cooley LLP

(57) ABSTRACT

The present invention provides a method of treating or preventing cardiac disorders in a subject in need thereof by inhibiting the expression or function of both miR-499 and miR-208 in the heart cells of the subject. In particular, specific protocols for administering inhibitors of the two miRNAs that achieve efficient, long-term suppression are disclosed. In addition, the invention provides a method for treating or preventing musculoskeletal disorders in a subject in need thereof by increasing the expression or activity of both miR-208 and miR-499 in skeletal muscle cells of the subject.

26 Claims, 9 Drawing Sheets

(56) References Cited

FOREIGN PATENT DOCUMENTS

| WO | WO 2008/074328 A2 | 6/2008 |
| WO | WO 2008/076324 A2 | 6/2008 |
| WO | WO 2008/147839 A1 | 12/2008 |
| WO | WO 2009/018492 A2 | 2/2009 |
| WO | WO 2009/026576 A1 | 2/2009 |
| WO | WO 2009/043353 A2 | 4/2009 |
| WO | WO 2009/058818 A2 | 5/2009 |
| WO | WO 2009/062169 A2 | 5/2009 |
| WO | WO 2009/114681 A2 | 9/2009 |
| WO | WO 2009/149182 A1 | 12/2009 |
| WO | WO 2010/048585 A2 | 4/2010 |

OTHER PUBLICATIONS

Landgraf et al., "A mammalian microRNA expression atlas based on small RNA library sequencing," Cell, Supplementary Table S12, 2007.

Van Rooij et al., "Control of stress-dependent cardiac growth and gene expression by a microRNA," Science, vol. 316: 575-579, 2007.

Habedanck, Supplementary European Search Report for European Application No. 08797004.2, 13 pages, European Patent Office, Munich, mailed Sep. 16, 2011.

Lorell et al., "Left Ventricular Hypertrophy: Pathogenesis, Detection, and Prognosis," Circulation, vol. 102:470-479, 2000.

Olson, "Transcriptional Control of Heart Development and Disease," Symposium Presentation at Duke University, Sep. 26, 2006.

Olson, Genetic Pathways in Cardiovascular Development and Disease, Symposium Presentation at University of Cincinnati, Sep. 2006.

Agrawal et al., "Antisense therapeutics: is it as simple as complementary base recognition?" Molecular Med. Today, vol. 6: 72-81 (2000).

Cheng et al., "MicroRNAs Are Aberrantly Expressed in Hypertrophic Heart," Am. J. Pathol. 170(6):1831-1840 (2007).

Chirila et al., "The use of synthetic polymers for delivery of therapeutic antisense oligodeoxynucleotides," Biomaterials, vol. 23: 321-342 (2002).

Crooke, "Progression in antisense technology," Ann. Rev. Medicine, vol. 55: 61-95 (2004).

Jang et al., "Gene delivery from polymer scaffolds for tissue engineering," Expert Rev. Medical Devices, vol. 1(1):127-138 (2004).

Opalinska et al., "Nucleic-acid therapeutics: basic prinicples and recent applications," Nature Rev., vol. 1:503-514 (2002).

Peracchi, "Prospects for antiviral ribozymes and deoxyribozymes," Rev. Med. Virol., vol. 14: 47-64 (2004).

Sayed et al., "MicroRNAs Play and Essential Role in the Development of Cardiac Hypertrophy," Circ. Res. 100(3):416-424 (2007).

Tatsuguchi et al., "Expression of MicroRNAs is Dynamically Regulated During Cardiomyocyte Hypertrophy," J. Mol. Cell. Cardiol. 42(6):1137-1141 (2007).

Thum et al., "MicroRNAs in the human Heart. A Clue to Fetal Gene Reprogramming in Heart Failure," Circulation 116(3):258-267 (2007).

Van Rooij et al., "Toward microRNA based therapeutics for heart disease: the sense in antisense," Circ. Res., vol. 103:919-928 (2008).

Copenheaver, "International Search Report and Written Opinion," 6 pages, International Application No. PCT/US2010/023234, U.S. Patent Office, Alexandria, VA, mailed Apr. 13, 2010.

Chen et al., "microRNAs and muscle disorders," Journal of Cell Science, vol. 122:13-20, 2008.

Van Rooij et al., "Myosin genes encode a network of microRNAs that control myosin expression and myofiber identity," Circulation, vol. 118: S305, 2008.

Macchia, Supplementary European Search Report for European Application No. 10739137.7, 8 pages, European Patent Office, The Hague, mailed Jul. 10, 2013.

FIGURE 4
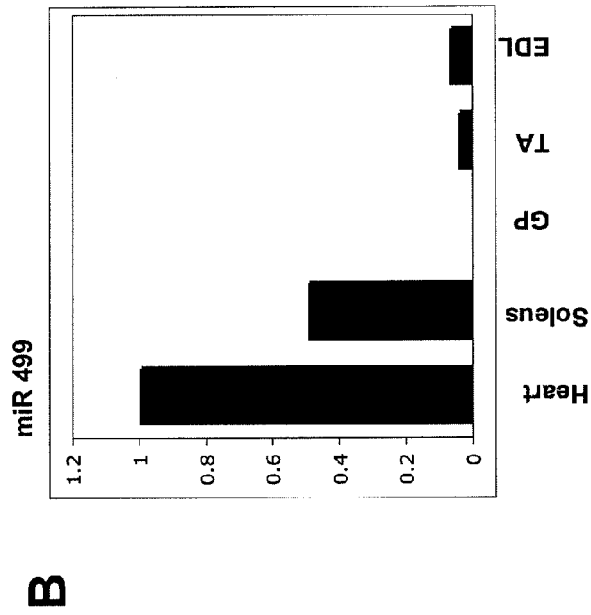
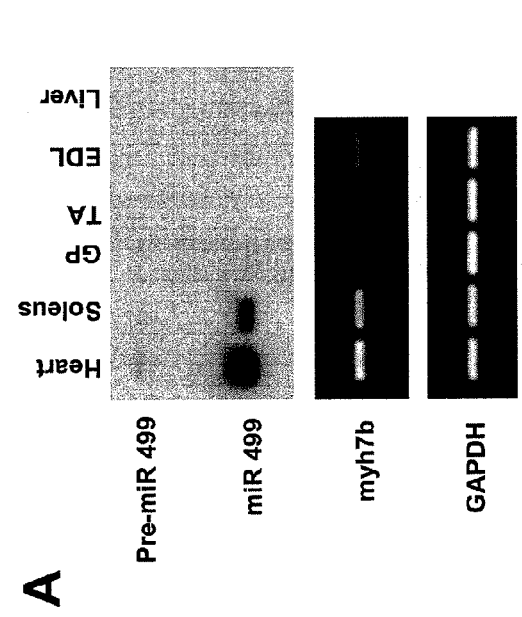
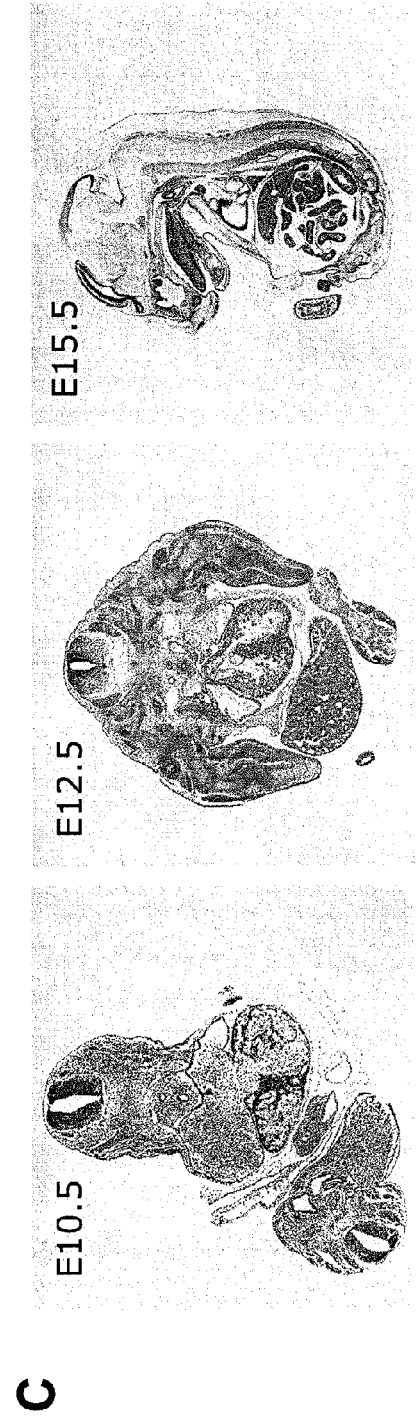

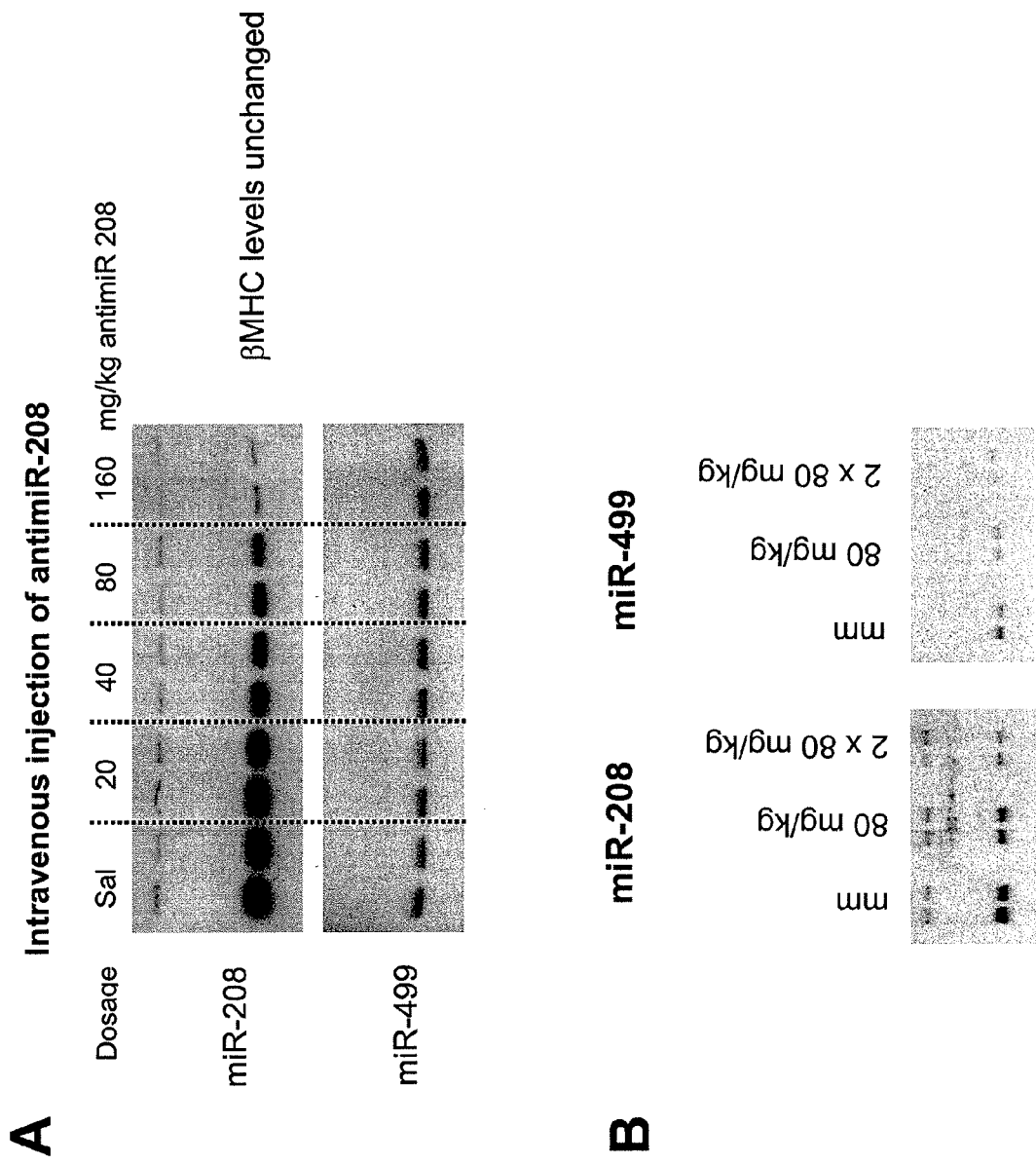
FIGURE 6A & B

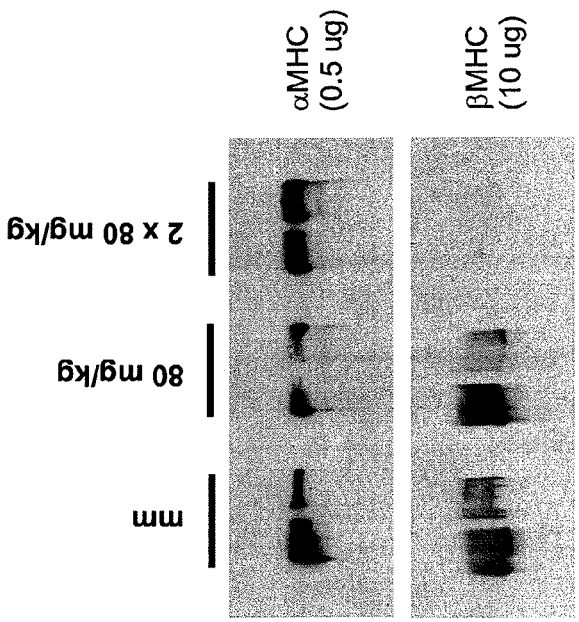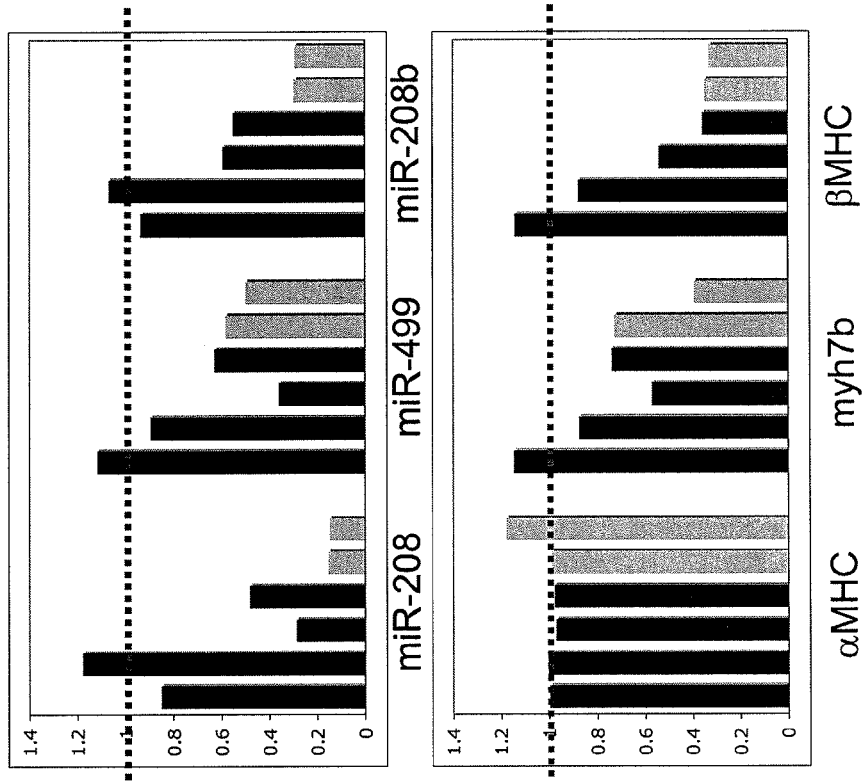
FIGURE 6C & D

SEQUENCE LISTING

```
<160> NUMBER OF SEQ ID NOS: 19

<210> SEQ ID NO 1
<211> LENGTH: 71
<212> TYPE: DNA
<213> ORGANISM: Homo sapiens

<400> SEQUENCE: 1
acgggcgagc ttttggcccg ggttatacct gatgctcacg tataagacga gcaaaaagct      60
tgttggtcag a                                                          71

<210> SEQ ID NO 2
<211> LENGTH: 71
<212> TYPE: DNA
<213> ORGANISM: Mus sp.

<400> SEQUENCE: 2
acgggtgagc ttttggcccg ggttatacct gactctcacg tataagacga gcaaaaagct      60
tgttggtcag a                                                          71

<210> SEQ ID NO 3
```

-continued

```
<211> LENGTH: 71
<212> TYPE: DNA
<213> ORGANISM: Rattus sp.

<400> SEQUENCE: 3
acgggtgagc ttttggcccg ggttatacct gactctcacg tataagacga gcaaaaagct    60
tgttggtcag a                                                          71

<210> SEQ ID NO 4
<211> LENGTH: 71
<212> TYPE: DNA
<213> ORGANISM: Canis sp.

<400> SEQUENCE: 4
acgcatgagc ttttggctcg ggttatacct gatgctcacg tataagacga gcaaaaagct    60
tgttggtcag a                                                          71

<210> SEQ ID NO 5
<211> LENGTH: 22
<212> TYPE: RNA
<213> ORGANISM: Unknown
<220> FEATURE:
<223> OTHER INFORMATION: mature miR-208

<400> SEQUENCE: 5
auaagacgag caaaaagcuu gu                                              22

<210> SEQ ID NO 6
<211> LENGTH: 76
<212> TYPE: DNA
<213> ORGANISM: Mus sp.

<400> SEQUENCE: 6
tccctgtgtc ttgggtgggc agctgttaag acttgcagtg atgtttagct cctctgcatg    60
tgaacatcac agcaag                                                     76

<210> SEQ ID NO 7
<211> LENGTH: 74
<212> TYPE: DNA
<213> ORGANISM: Rattus sp.

<400> SEQUENCE: 7
tccctgtctt gggtgggcag ctgttaagac ttgcagtgat gtttagctcc tctccatgtg    60
aacatcacag caag                                                       74

<210> SEQ ID NO 8
<211> LENGTH: 76
<212> TYPE: DNA
<213> ORGANISM: Homo sapiens

<400> SEQUENCE: 8 ccctgtgcc ttgggcgggc ggctgttaag acttgcagtg atgtttaact cctctccacg     60
tgaacatcac agcaag                                                     76

<210> SEQ ID NO 9
<211> LENGTH: 76
<212> TYPE: DNA
<213> ORGANISM: Canis sp.

<400> SEQUENCE: 9
cccttgcacc ctgggcgggc ggccgttaag acttgcagtg atgtttaact cctctccacg    60
```

```
tgaacatcac agcaag                                              76

<210> SEQ ID NO 10
<211> LENGTH: 76
<212> TYPE: DNA
<213> ORGANISM: Didelphis sp.

<400> SEQUENCE: 10
cccctgcctc cccggcgggc agctgttaag acttgcagtg atgtttaatt cttctctatg    60
tgaacatcac aacaag                                              76

<210> SEQ ID NO 11
<211> LENGTH: 62
<212> TYPE: DNA
<213> ORGANISM: Gallus sp.

<400> SEQUENCE: 11
ggagcggcag ttaagacttg tagtgatgtt tagataatgt attacatgga catcacttta    60
ag                                                             62

<210> SEQ ID NO 12
<211> LENGTH: 68
<212> TYPE: DNA
<213> ORGANISM: Xenopus tropicalis

<400> SEQUENCE: 12
gtcttagcga ggcagttaag acttgcagtg atgtttagtt aaaatctttt catgaacatc    60
actttaag                                                       68

<210> SEQ ID NO 13
<211> LENGTH: 79
<212> TYPE: RNA
<213> ORGANISM: Mus sp.

<400> SEQUENCE: 13 ggguggggcag cuguuaagac uugcagugau guuuagcucc ucugcaugug aacaucacag    60
caagucugug cugcugccu                                           79

<210> SEQ ID NO 14
<211> LENGTH: 21
<212> TYPE: RNA
<213> ORGANISM: Unknown
<220> FEATURE:
<223> OTHER INFORMATION: mature miR-499

<400> SEQUENCE: 14
uuaagacuug cagugauguu u                                        21

<210> SEQ ID NO 15
<211> LENGTH: 22
<212> TYPE: RNA
<213> ORGANISM: Artificial Sequence
<220> FEATURE:
<223> OTHER INFORMATION: miR-208 antagomir

<400> SEQUENCE: 15
acaagcuuuu ugcucgucuu au                                       22

<210> SEQ ID NO 16
<211> LENGTH: 22
<212> TYPE: RNA
<213> ORGANISM: Artificial Sequence
<220> FEATURE:
```

```
<223> OTHER INFORMATION: antimiR-208 oligonucleotide
<220> FEATURE:
<221> NAME/KEY: misc_feature
<222> LOCATION: (1)..(22)
<223> OTHER INFORMATION: May be 2'-OMe modified oligonucleosides
<220> FEATURE:
<221> NAME/KEY: misc_feature
<222> LOCATION: (1)..(2)
<223> OTHER INFORMATION: May contain phosphorothioate internucleoside
      linkages
<220> FEATURE:
<221> NAME/KEY: misc_feature
<222> LOCATION: (19)..(22)
<223> OTHER INFORMATION: May contain phosphorothioate internucleoside
      linkages

<400> SEQUENCE: 16
acaagcuuuu ugcucgucuu au                                              22

<210> SEQ ID NO 17
<211> LENGTH: 22
<212> TYPE: RNA
<213> ORGANISM: Artificial Sequence
<220> FEATURE:
<223> OTHER INFORMATION: mismatch miR-208 oligonucleotide
<220> FEATURE:
<221> NAME/KEY: misc_feature
<222> LOCATION: (1)..(22)
<223> OTHER INFORMATION: May be 2'-OMe modified oligonucleosides
<220> FEATURE:
<221> NAME/KEY: misc_feature
<222> LOCATION: (1)..(2)
<223> OTHER INFORMATION: May contain phosphorothioate internucleoside
      linkages
<220> FEATURE:
<221> NAME/KEY: misc_feature
<222> LOCATION: (19)..(22)
<223> OTHER INFORMATION: May contain phosphorothioate internucleoside
      linkages

<400> SEQUENCE: 17
accagcuuug ugcucguaug au                                              22

<210> SEQ ID NO 18
<211> LENGTH: 43
<212> TYPE: DNA
<213> ORGANISM: Unknown
<220> FEATURE:
<223> OTHER INFORMATION: pre-miR-208b

<400> SEQUENCE: 18
tttctgatcc gaatataaga cgaacaaaag gtttgtctga ggg                       43

<210> SEQ ID NO 19
<211> LENGTH: 22
<212> TYPE: RNA
<213> ORGANISM: Unknown
<220> FEATURE:
<223> OTHER INFORMATION: mature miR-208b

<400> SEQUENCE: 19
auaagacgaa caaaagguuu gu                                              22
```

DUAL TARGETING OF MIR-208 AND MIR-499 IN THE TREATMENT OF CARDIAC DISORDERS

CROSS-REFERENCE TO RELATED APPLICATIONS

This application is a national stage application of International Application No. PCT/US2010/023234, filed Feb. 4, 2010, which claims the benefit of U.S. Provisional Application No. 61/149,915, filed Feb. 4, 2009, both of which is are herein incorporated by reference in their entireties.

STATEMENT OF GOVERNMENT SUPPORT

This invention was made with government support under Grant Number HL53351-06 awarded by the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_013_01WO_SeqList_ST25.txt, date recorded: Feb. 1, 2010, file size 5 kilobytes).

FIELD OF THE INVENTION

The present invention relates to the treatment of cardiac and musculoskeletal disorders by administering agents that modulate the activity or expression of microRNAs (miRNAs). In particular, the invention provides a method for treating or preventing cardiac disorders by inhibiting the expression or activity of both miR-208a/miR-208b and miR-499 in the heart cells of a subject, including humans. In addition, the invention provides a method for treating or preventing musculoskeletal disorders by increasing the expression or activity of both miR-208b and miR-499 in skeletal muscle cells of a subject.

BACKGROUND OF THE INVENTION

Heart disease and its manifestations, including coronary artery disease, myocardial infarction, congestive heart failure and cardiac hypertrophy, clearly present a major health risk in the United States today. The cost to diagnose, treat and support patients suffering from these diseases is well into the billions of dollars. Two particularly severe manifestations of heart disease are myocardial infarction and cardiac hypertrophy.

Myocardial infarction, commonly known as a heart attack, is caused by a sudden and sustained lack of blood flow to the heart tissue, which is usually the result of a narrowing or occlusion of a coronary artery. Without adequate blood supply, the tissue becomes ischemic, leading to the death of cardiomyocytes (e.g. heart muscle cells) and vascular structures. The necrotic tissue resulting from the death of the cardiomyocytes is generally replaced by scar tissue, which is not contractile, fails to contribute to cardiac function, and often plays a detrimental role in heart function by expanding during cardiac contraction, or by increasing the size and effective radius of the ventricle, for example, becoming hypertrophic.

Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy (DCM), heart failure, and sudden death. In the United States, approximately half a million individuals are diagnosed with heart failure each year, with a mortality rate approaching 50%.

Numerous signaling pathways, especially those involving aberrant calcium signaling, drive cardiac hypertrophy and pathological remodeling (Heineke & Molkentin, 2006). Hypertrophic growth in response to stress involves different signaling pathways and gene expression patterns than physiological hypertrophy, which occurs in response to exercise. Stress-mediated myocardial hypertrophy is a complex phenomenon associated with numerous adverse consequences with distinct molecular and histological characteristics causing the heart to fibrose, dilate and decompensate which, through cardiomyocyte degeneration and death, often culminates in heart failure. As such, there has been intense interest in deciphering the underlying molecular mechanisms and in discovering novel therapeutic targets for suppressing adverse cardiac growth and ultimately failure. Understanding these mechanisms is essential to the design of new therapies to treat cardiac hypertrophy and heart failure.

MicroRNAs have recently been implicated in a number of biological processes including regulation of developmental timing, apoptosis, fat metabolism, and hematopoietic cell differentiation among others. MicroRNAs (miRNAs) are small, non-protein coding RNAs of about 18 to about 25 nucleotides in length that are derived from individual miRNA genes, from introns of protein coding genes, or from polycistronic transcripts that often encode multiple, closely related miRNAs. See review by Carrington et al. (*Science*, Vol. 301(5631):336-338, 2003). MiRNAs act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al. (2006) *Cellular & Molecular Immunology*, Vol. 3:411-419) and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

Recently, the inventors reported a cardiac-specific microRNA, miR-208a, which is encoded by an intron of the α-myosin heavy chain (MHC) gene, and is required for up-regulation of β-MHC expression in response to cardiac stress and for repression of fast skeletal muscle genes in the heart (van Rooij et al., (2007) *Science*, Vol. 316: 575-579). The present invention expands on this discovery and provides a novel therapeutic approach to the treatment of cardiac and musculoskeletal disorders.

SUMMARY OF THE INVENTION

The present invention is based, in part, on the discovery that systematic downregulation of both miR-208a and miR-499 in heart cells produces a synergistic effect on the development of cardiac hypertrophy, enhanced contractility, and pathological cardiac remodeling in response to stress. The inventors have surprisingly found that the time period for regulating expression of stress-related genes, such as β-MHC, is dramatically decreased by downregulating both miR-208a and miR-499 by either simultaneous or sequential administration of miR-208a and miR-499 inhibitors. Such dual targeting produces immediate effects on stress-related gene expression as compared to the several month delay required to observe similar effects with downregulation of miR-208a alone. Accordingly, the present invention provides a novel therapeutic approach for the treatment of pathologic cardiac hypertrophy, heart failure, and myocardial infarction in a subject in need thereof, including a human.

In one embodiment, the method comprises administering an inhibitor of miR-208a or miR-208b and an inhibitor of miR-499 to a subject, wherein the expression or activity of miR-208a or miR-208b and miR-499 is reduced in the heart cells of the subject following administration. In some embodiments, the expression or activity of miR-208a or miR-208b and miR-499 is reduced by greater than 60 percent in the heart cells of the subject following administration of the inhibitors. The miR-208 and miR-499 inhibitors include antagomirs or antisense oligonucleotides. In one embodiment, the miRNA inhibitors are encoded on a expression vector.

In another embodiment, the cardiac stress response is reduced in the subject following administration of an inhibitor of miR-208a or miR-208b and an inhibitor of miR-499. The cardiac stress response includes hypertrophy of cardiomyocytes, fibrosis of the heart, reduced expression of α-MHC, and/or increased expression of β-MHC in the heart cells of said subject. In certain embodiments, the reduction of the cardiac stress response occurs less than two months after administration of the miR-208a/miR-208b and miR-499 inhibitors. In a preferred embodiment, the reduction of the cardiac stress response occurs less than one week after administration of the inhibitors.

In some embodiments, the miR-208a/miR-208b inhibitor and the miR-499 inhibitor are administered sequentially. Administration of the two inhibitors can be separated by an interval that can be on the order of minutes to weeks. In one embodiment, the miR-208a/miR-208b inhibitor and the miR-499 inhibitor are administered at least 24 hours apart. In another embodiment, the miR-208a/miR-208b inhibitor and the miR-499 inhibitor are co-administered. The two inhibitors can be administered each at a dosage of about 1 mg/kg to about 200 mg/kg.

The present invention also provides a method of treating or preventing a musculoskeletal disorder in a subject in need thereof comprising administering an agonist of miR-208 and an agonist of miR-499 to the subject, wherein the expression or activity of miR-208 and miR-499 is increased in the skeletal muscle cells of the subject following administration. In one embodiment, the method comprises administering an agonist of miR-208b and an agonist of miR-499 to the subject. The miRNA agonists can be polynucleotides encoding mature miR-208a, miR-208b, or miR-499 sequences. In some embodiments, such polynucleotides are operably linked to a promoter sequence and provided to the subject's cells in an expression vector.

The miRNA agonists may be co-administered or administered sequentially separated by a particular time interval. In some embodiments, the expression of one or more fast skeletal muscle genes in the skeletal muscle cells of a subject is reduced following administration of the miR-499 and miR-208a or miR-208b agonists to the subject. One or more fast skeletal muscle genes can include troponin I2, troponin T3, fast skeletal myosin light chain, and alpha skeletal actin.

BRIEF DESCRIPTION OF THE DRAWINGS

FIG. 4. Myh7b and miR-499 are expressed in cardiac and slow skeletal muscle. A. Northern analysis indicates that miR-499 is expressed in heart and slow skeletal muscle (e.g. soleus). RT-PCR for Myh7b shows that miR-499 is co-expressed with its hostgene. B. Real-time PCR analysis for miR-499 on heart and four skeletal muscle types (gastrocnemius/plantaris (GP), tibialis anterior (TA), extensor digitorum longus (EDL), and soleus) confirms that miR-499 is predominantly expressed in the heart and soleus. Only minor levels of miR-499 expression can be detected in TA and EDL. C. In situ hybridization indicates that during embryogenesis, Myh7b is specifically expressed in the heart and somites.

FIG. 6. The regulation of miR-499 by in vivo knockdown of miR-208. A. Northern analysis of miR-208 and miR-499 expression three days after tail vein injection of the indicated amount of anti-miR-208 oligonucleotide or saline (Sal). B. Northern analysis for miR-208 and miR-499 expression of cardiac tissue of animals injected with either a single 80 mg/kg dose of anti-miR-208, 2×80 mg/kg doses of anti-miR-208 on two consecutive days, or a mismatched control oligonucleotide (mm) two months after treatment. C. Realtime PCR analysis for miR-208, miR-499, miR-208b, α-MHC, Myh7b, and β-MHC expression in cardiac tissue two months after treatment with a single dose of anti-miR-208, two doses of anti-miR-208 on two consecutive days, or two doses of a mismatched oligonucleotide on two consecutive days. D. Western blot analysis of β-MHC expression in cardiac tissue two months after anti-miR-208 (single 80 mg/kg dose or two consecutive 80 mg/kg doses) or mismatch (mm) control treatment.

DETAILED DESCRIPTION OF THE INVENTION

Figure 1:
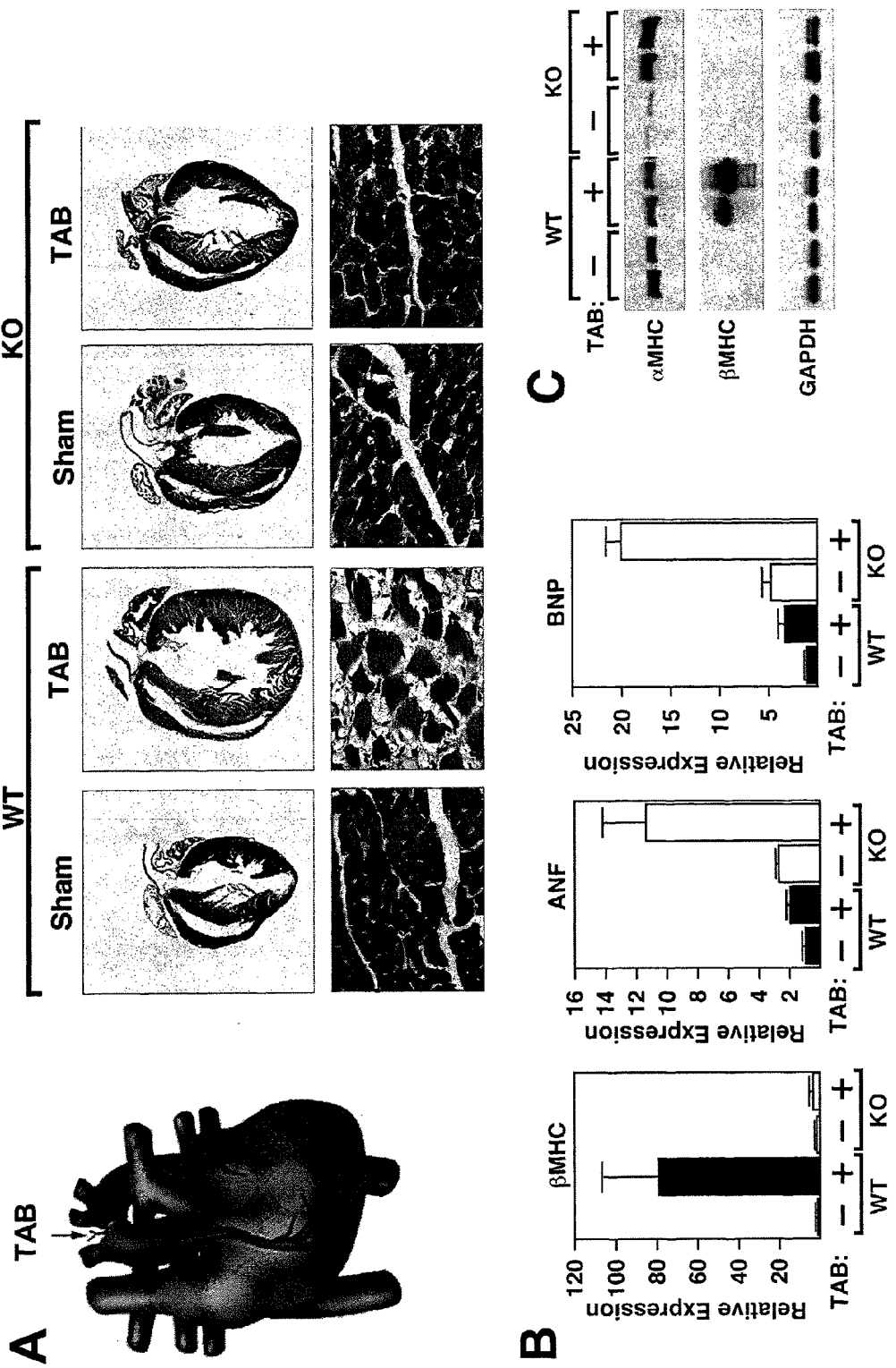
FIG. 1. MiR-208 knockout animals exhibit less cardiac hypertrophy and fibrosis in response to thoracic aortic banding. A. Schematic illustrating the thoracic aortic banding (TAB) procedure (left). Histological sections of hearts of wild-type and miR-208−/− mice stained for Masson trichrome after TAB procedure or sham procedure (right). The absence of miR-208 diminishes hypertrophy and fibrosis seen in wild-type mice subjected to TAB for 21 days. B. Relative expression levels for beta-myosin heavy chain (β-MHC), atrial natriuretic factor (ANF), and brain natriuretic peptide (BNP) in hearts of wild-type and miR-208−/− animals after a sham or TAB procedure. C. Western analysis of α-MHC and β-MHC protein levels in hearts of wild-type and miR-208−/− animals after a sham or TAB procedure. GAPDH was detected as a loading control.

Cardiac and skeletal muscles respond to a variety of pathophysiological stimuli such as workload, thyroid hormone signaling and injury by modulating the expression of myosin isoforms, which regulate the efficiency of contraction.

The ratio of α- to β-MHC isoforms in the adult heart is a major determinant of cardiac contractility. β-MHC, the major myosin isoform in the adult heart, displays relatively low ATPase activity, whereas α-MHC has high ATPase activity. In response to a variety of pathological stimuli such as myocardial infarction, hypertension, and other disorders, β-MHC expression increases, while α-MHC expression decreases with a consequent reduction in myofibrillar ATPase activity and reduced shortening velocity of cardiac myofibers, leading to eventual contractile dysfunction. Remarkably, minor changes in α-MHC content of the heart can have a profound influence on cardiac performance.

Recently, the inventors reported a cardiac-specific miRNA, miR-208a, which is encoded by an intron of the α-myosin heavy chain gene, and is required for up-regulation of β-MHC expression in response to cardiac stress and for repression of fast skeletal muscle genes in the heart (see co-pending application WO 2008/016924, which is herein incorporated by reference in its entirety).

The inventors have also recently discovered that miR-208a is also required for cardiac expression of a closely related miRNA, miR-499, which is encoded by an intron of the Myh7b gene (see co-pending application PCT/US08/71837, which is herein incorporated by reference in its entirety). Expression of Myh7b and miR-499 in the heart, as well as in slow skeletal muscle, is controlled by the MEF2 transcription factor, a signal-dependent regulator of striated muscle gene expression. Forced expression of miR-499 or miR-208 is sufficient to mediate a fast to slow myofiber conversion in vivo. MiR-208 and miR-499 can negatively regulate the expression of Thrap1, a thyroid hormone receptor coregulator, and members of the PUR family of transcription factors, which in turn negatively regulate β-MHC expression in cardiac and skeletal muscle. Sox6 functions as a repressor of slow fiber type-specific genes. Knockdown of Sox6 expression in wild-type myotubes results in a significant increase in β-MHC expression. Analysis of the β-MHC promoter revealed a Sox consensus sequence which suggests that Sox6 plays a critical role in the fiber type differentiation of fetal skeletal muscle and β-MHC regulation in the heart. These findings unveil a common regulatory mechanism in which Myh genes regulate the gene expression patterns of striated muscles by encoding regulatory miRNAs that govern contractility and signal responsiveness (van Rooij et al. (2009) Developmental Cell, Vol. 17: 662-673).

The present invention is based, in part, on the discovery that downregulation of both miR-208 and miR-499 in heart cells produces a synergistic effect in suppressing the cardiac stress response. Inhibition of miR-208a expression in heart cells results in a reduction of stress-induced expression of β-MHC. However, this effect is not observed until two months following administration of the miR-208 inhibitor. The inventors have surprisingly found that the inhibition of both miR-208a and miR-499 result in suppression of stress-induced β-MHC expression almost immediately after administration, thus accelerating the effect on the cardiac stress response. Accordingly, strategies to manipulate skeletal and cardiac muscle gene expression by modulating miR-208 and miR-499 expression, either simultaneously or sequentially, for the treatment and prevention of cardiac diseases are described in light of these discoveries.

MiR-208a is located within an intron of the α-MHC gene. The precise intron location is dependent on the particular species and specific transcript. For example, in humans, miR-208a is encoded within the 28$^{th}$ intron of the α-MHC gene, while in mice, it is encoded within the 29$^{th}$ intron. The pre-miRNA encoding sequences for miR-208a for human, mouse, rat, and canine are shown below as SEQ ID NO: 1, SEQ ID NO: 2, SEQ ID NO: 3, and SEQ ID NO: 4, respectively. The mature miR-208a sequence is provided in SEQ ID NO: 5. Like α-MHC, miR-208a is expressed solely in the heart.

```
Human pre-miR-208a
                                        (SEQ ID NO: 1)
ACGGGCGAGC TTTTGGCCCG GGTTATACCT GATGCTCACG

TATAAGACGA GCAAAAAGCT TGTTGGTCAG A

Mouse pre-miR-208a
                                        (SEQ ID NO: 2)
ACGGGTGAGC TTTTGGCCCG GGTTATACCT GACTCTCACG

TATAAGACGA GCAAAAAGCT TGTTGGTCAG A

Rat pre-miR-208a
                                        (SEQ ID NO: 3)
ACGGGTGAGC TTTTGGCCCG GGTTATACCT GACTCTCACG

TATAAGACGA GCAAAAAGCT TGTTGGTCAG A

Canine pre-miR-208a
```

```
                                                     (SEQ ID NO: 4)
ACGCATGAGC TTTTGGCTCG GGTTATACCT GATGCTCACG

TATAAGACGA GCAAAAAGCT TGTTGGTCAG A

Mature miR-208a
                                                     (SEQ ID NO: 5)
AUAAGACGAGCAAAAAGCUUGU
```

Analysis of the genomic location of the miR-499 gene showed it to be contained within the 20th intron of the Myh7b gene, a homolog of the α-MHC gene. The pre-miRNA encoding sequences for miR-499 for mouse, rat, human, canine, opposum, chicken and *X. tropicalis* are provided in SEQ ID NO: 6, SEQ ID NO: 7, SEQ ID NO: 8, SEQ ID NO: 9, SEQ ID NO: 10, SEQ ID NO: 11 and SEQ ID NO: 12, respectively. SEQ ID NO: 13 is the stem-loop structure of the mouse precursor sequence and SEQ ID NO: 14 is the mature miR-499 sequence. The Myh7b gene is conserved in vertebrates and is expressed solely in the heart and slow skeletal muscle (e.g. soleus).

```
    Mouse pre-miR-499
                                                     (SEQ ID NO: 6)
    TCCCTGTGTC TTGGGTGGGC AGCTGTTAAG ACTTGCAGTG

ATGTTTAGCT CCTCTGCATG TGAACATCAC AGCAAG

Rat pre-miR-499
                                                     (SEQ ID NO: 7)
    TCCCTGTCTT GGGTGGGCAG CTGTTAAGAC TTGCAGTGAT

GTTTAGCTCC TCTCCATGTG AACATCACAG CAAG

Human pre-miR-499
                                                     (SEQ ID NO: 8)
    CCCCTGTGCC TTGGGCGGGC GGCTGTTAAG ACTTGCAGTG

ATGTTTAACT CCTCTCCACG TGAACATCAC AGCAAG

Canine pre-miR-499
                                                     (SEQ ID NO: 9)
    CCCTTGCACC CTGGGCGGGC GGCCGTTAAG ACTTGCAGTG

ATGTTTAACT CCTCTCCACG TGAACATCAC AGCAAG

Opposum pre-miR-499
                                                     (SEQ ID NO: 10)
    CCCCTGCCTC CCCGGCGGGC AGCTGTTAAG ACTTGCAGTG

ATGTTTAATT CTTCTCTATG TGAACATCAC AACAAG

Chicken pre-miR-499
                                                     (SEQ ID NO: 11)
    GGAGCGGCAG TTAAGACTTG TAGTGATGTT TAGATAATGT

ATTACATGGA CATCACTTTA AG

X. tropicalis pre-miR-499
                                                     (SEQ ID NO: 12)
    GTCTTAGCGA GGCAGTTAAG ACTTGCAGTG ATGTTTAGTT

AAAATCTTTT CATGAACATC ACTTTAAG

Mouse stem-loop of the pre-miR-499 sequence
                                                     (SEQ ID NO: 13)
    GGGUGGGCAG CUGUUAAGAC UUGCAGUGAU GUUUAGCUCC

UCUGCAUGUG AACAUCACAG CAAGUCUGUG CUGCUGCCU

Mature miR-499
                                                     (SEQ ID NO: 14)
    UUAAGACUUG CAGUGAUGUU U
```

The inventors have also discovered that the genome contains a second version of miR208a, called miR-208b, which is located within the β-MHC gene at intron 31, and like β-MHC, miRNA 208b is expressed solely in the heart and slow skeletal muscle (e.g. soleus). Genes regulated by miR-208b include, for example, Sp3, Myostatin, PURbeta, THRAP1, and fast skeletal muscle protein genes. The sequence of this miRNA is largely overlapping with miR-208a with a 100% homology in the "seed region," the region that defines mRNA targets of a certain miRNA. Thus, miR-208b can have profound effects on cardiac and skeletal muscle contractility in humans. The pre-miR-208b sequence is conserved across several mammalian species (e.g. human, mouse, rat, and canine). The pre-miR-208b sequence as well as the mature miR-208b sequence is shown below:

```
pre-miR-208b
                                                     (SEQ ID NO: 18)
TTTCTGATCC GAATATAAGA CGAACAAAAG GTTTGTCTGA GGG Mature miR-208b
                                                     (SEQ ID NO: 19)
AUAAGACGAA CAAAAGGUUU GU
```

It is understood that when the RNA sequences disclosed herein are used in embodiments that require deoxyribonucleotides, a thymidine residue is substituted for a uridine residue. Similarly, in embodiments requiring ribonucleotides, a uridine residue is substituted for a thymidine residue in the DNA sequences disclosed herein.

In one embodiment, the present invention provides a method of treating pathologic cardiac hypertrophy, myocardial infarction, or heart failure in a subject in need thereof, including a human, by targeting the expression and/or activity of either or both miR-208 (e.g., miR-208a and/or miR-208b, or in other words, miR208a/miR208b) and miR-499 in the heart cells of the subject. In some embodiments, an inhibitor of miR-208a/miR-208b and an inhibitor of miR-499 are administered to the subject to reduce the expression or activity of miR-208a/miR-208b and miR-499 in the heart cells of the subject.

In another embodiment, the subject in need thereof may be at risk for developing pathologic cardiac hypertrophy, heart failure, or myocardial infarction. Such a subject may exhibit one or more risk factors including, but not limited to, long standing uncontrolled hypertension, uncorrected valvular disease, chronic angina, recent myocardial infarction, congenital predisposition to heart disease or pathological hypertrophy. The subject at risk may be diagnosed as having a genetic predisposition to cardiac hypertrophy or may have a familial history of cardiac hypertrophy.

Preferably, administration of both an inhibitor of miR-208a/miR-208b and an inhibitor of miR-499 to the subject results in the improvement of one or more symptoms of cardiac hypertrophy, heart failure, or myocardial infarction in the subject, or in the delay in the transition from cardiac hypertrophy to heart failure. The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease related morbidity or mortality.

In one embodiment of the invention, the cardiac stress response is reduced in the subject following administration of the miR-208 (e.g., miR-208a and/or miR-208b) and miR-499 inhibitors. The cardiac stress response includes, inter alia, cardiomyocyte hypertrophy, fibrosis of the heart, reduced expression of α-MHC in the heart cells, and/or increased expression of β-MHC in the heart cells. Administration of both an inhibitor of miR-208a/miR-208b and an inhibitor of miR-499 to the subject results in a more rapid effect on the cardiac stress response as compared to administration of either inhibitor alone. For instance, the reduction of the cardiac stress response occurs less than eight weeks, less than six weeks, less than four weeks, less than three weeks, less than two weeks, less than one week, less than five days, less than three days, or less than one day following administration of the inhibitors. In another embodiment, the reduction in the cardiac stress response occurs less than twelve hours following administration of the inhibitors.

In some embodiments, miR-208 (e.g., miR-208a and/or miR-208b) and miR-499 inhibitors may be antisense oligonucleotides targeting the mature miR-499 and/or miR-208a or miR-208b sequences. The antisense oligonucleotides may be ribonucleotides or deoxyribonucleotides. Preferably, the antisense oligonucleotides have at least one chemical modification. For instance, suitable antisense oligonucleotides may be comprised of one or more "conformationally constrained" or bicyclic sugar nucleoside modifications, for example, "locked nucleic acids." "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. The antisense oligonucleotides targeting miR-208a/miR-208b and miR-499 can contain combinations of LNAs or other modified nucleotides and ribonucleotides or deoxyribonucleotides. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). For instance, antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O alkyl and the like. In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Preferable antisense oligonucleotides useful for inhibiting the activity of miRNAs are about 5 to about 50 nucleotides in length, about 10 to about 30 nucleotides in length, or about 20 to about 25 nucleotides in length. In certain embodiments, antisense oligonucleotides targeting miR-208a/miR-208b and miR-499 are about 8 to about 18 nucleotides in length, and in other embodiments about 12 to 16 nucleotides in length. In particular, any 8-mer or longer that is complementary to miR208a or miR208b may be used, i.e., any antimir sequence that is complementary to any consecutive sequence in miR208a or miR208b, starting from the 5' end of the miR to the 3' end of the mature sequence. Antisense oligonucleotides may in some cases comprise a sequence that is at least partially complementary to a mature miRNA sequence, e.g. at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the antisense oligonucleotide comprises a sequence that is 100% complementary to a mature miRNA sequence.

In other embodiments, the antisense oligonucleotides are antagomirs. "Antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a steroid such as cholesterol, a fatty acid, a vitamin, a carbohydrate, a peptide or another small molecule ligand at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

In some embodiments, inhibitors of miR-499 and miR-208a/miR-208b are antagomirs comprising a sequence that is perfectly complementary to the mature miR-499 and mature miR-208a or miR-208b sequence. In one embodiment, an inhibitor of miR-499 is an antagomir having a sequence that is partially or perfectly complementary to 5'-UUAAGACU-UGCAGUGAUGUUU-3' (SEQ ID NO: 14). In another embodiment, an inhibitor of miR-208a is an antagomir having a sequence that is partially or perfectly complementary to 5'-AUAAGACGAGCAAAAAGCUUGU-3' (SEQ ID NO: 5). In another embodiment, an inhibitor of miR-208a is an antagomir having the sequence 5'-ACAAGCU-UUUUGCUCGUCUUAU-3' (SEQ ID NO: 15). In still another embodiment, an inhibitor of miR-208a is an antagomir having the sequence of SEQ ID NO: 16. In another embodiment, an inhibitor of miR-208b is an antagomir having a sequence that is partially or perfectly complementary to 5'-AUAAGACGAACAAAAGGUUUGU-3' (SEQ ID NO: 19).

In some embodiments, inhibitors of miR-499 and miR-208a or miR-208b are chemically-modified antisense oligonucleotides. In one embodiment, an inhibitor of miR-499 is a chemically-modified antisense oligonucleotide comprising a sequence substantially complementary to 5'-UUAAGACU-UGCAGUGAUGUUU-3' (SEQ ID NO: 14). In another embodiment, an inhibitor of miR-208a is a chemically-modified antisense oligonucleotide comprising a sequence substantially complementary to 5'-AUAAGACGAG-CAAAAAGCUUGU-3' (SEQ ID NO: 5). In yet another embodiment, an inhibitor of miR-208b is a chemically-modified antisense oligonucleotide comprising a sequence substantially complementary to 5'-AUAAGACGAACAAAAG-GUUUGU-3' (SEQ ID NO: 19). As used herein "substantially complementary" refers to a sequence that is at least about 95%, 96%, 97%, 98%, 99%, or 100% complementary to a target polynucleotide sequence (e.g. mature or precursor miRNA sequence).

Antisense oligonucleotides may comprise a sequence that is substantially complementary to a precursor miRNA sequence (pre-miRNA) for miR-499 or miR-208a/miR-208b. In some embodiments, the antisense oligonucleotide comprises a sequence that is substantially complementary to a sequence located outside the stem-loop region of the pre-miR-499 or pre-miR-208a/miR-208b sequence. In one embodiment, an inhibitor of miR-499 function is an antisense oligonucleotide having a sequence that is substantially complementary to a pre-miR-499 sequence selected from the group consisting of SEQ ID NO: 6, SEQ ID NO: 7, SEQ ID NO: 8, SEQ ID NO: 9, SEQ ID NO: 10, SEQ ID NO: 11 and SEQ ID NO: 12. In another embodiment, an inhibitor of miR-208a function is an antisense oligonucleotide having a sequence that is substantially complementary to a pre-miR-208a sequence selected from the group consisting of SEQ ID NO: 1, SEQ ID NO: 2, SEQ ID NO: 3, and SEQ ID NO: 4. In still another embodiment, an inhibitor of miR-208b function is an antisense oligonucleotide having a sequence that is substantially complementary to a pre-miR-208b sequence of SEQ ID NO: 18.

In another embodiment of the invention, a single nucleic acid molecule may be used to inhibit both miR-208 and miR-499 simultaneously. For instance, a single nucleic acid may contain a sequence that is at least partially complementary to a mature miR-208a sequence (e.g. SEQ ID NO: 5) and a sequence that is at least partially complementary to a mature miR-499 sequence (e.g. SEQ ID NO: 14). In another embodiment, a single nucleic acid may contain a sequence that is at least partially complementary to a mature miR-208b sequence (e.g. SEQ ID NO: 19) and a sequence that is at least partially complementary to a mature miR-499 sequence (e.g. SEQ ID NO: 14). In yet another embodiment, the single nucleic acid molecule may contain a sequence that is at least partially complementary to a pre-miR-208a sequence (e.g. SEQ ID NO: 1, SEQ ID NO: 2, SEQ ID NO: 3, and SEQ ID NO: 4) and a sequence that is at least partially complementary to a pre-miR-499 sequence (e.g. SEQ ID NO: 6, SEQ ID NO: 7, SEQ ID NO: 8, SEQ ID NO: 9, SEQ ID NO: 10, SEQ ID NO: 11 and SEQ ID NO: 12). In another embodiment, the single nucleic acid molecule may contain a sequence that is at least partially complementary to a pre-miR-208b sequence (e.g. SEQ ID NO: 18) and a sequence that is at least partially complementary to a pre-miR-499 sequence (e.g. SEQ ID NO: 6, SEQ ID NO: 7, SEQ ID NO: 8, SEQ ID NO: 9, SEQ ID NO: 10, SEQ ID NO: 11 and SEQ ID NO: 12). The single nucleic acid molecule may further comprise one or more spacer nucleotides between the miR-208 (e.g., miR-208a or miR-208b) and miR-499 targeting sequences. For instance, the single nucleic acid molecule may contain about 1 to about 200 spacer nucleotides, more preferably about 5 to about 100 spacer nucleotides, most preferably about 10 to about 50 spacer nucleotides between the miR-208a/miR-208b and miR-499 targeting sequences.

Any of the inhibitors of miR-208a/miR-208b and miR-499 described herein can be delivered to the target cell (e.g. heart cell, skeletal muscle cell) by delivering to the cell an expression vector encoding the miR-208a/miR-208b and miR-499 inhibitors. The inhibitor of miR-208a/miR-208b and the inhibitor of miR-499 can be encoded by the same expression vector. Alternatively, the inhibitor of miR-208 (e.g., miR-208a or miR-208b) and the inhibitor of miR-499 are encoded on separate expression vectors. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an inhibitor of miR-208a/miR-208b and/or miR-499 comprises a promoter operably linked to a polynucleotide encoding an antisense oligonucleotide, wherein the sequence of the expressed antisense oligonucleotide is partially or perfectly complementary to a mature sequence of miR-208 (e.g., miR-208a or miR-208b) and/or miR-499. The phrase "operably linked" or "under transcriptional control" as used herein means that the promoter is in the correct location and orientation in relation to a polynucleotide to control the initiation of transcription by RNA polymerase and expression of the polynucleotide. In another embodiment, the expression vector may encode a single nucleic acid that targets both miR-208 (e.g., miR-208a or miR-208b) and miR-499 as described herein, wherein the single nucleic acid is operably linked to a promoter. In another embodiment, a single expression vector may encode a miR-208a/miR-208b inhibitor and a miR-499 inhibitor, wherein the miR-208a/miR-208b inhibitor is driven by a different promoter than the miR-499 inhibitor.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, poi II, pol III, and viral promoters (e.g. human cytomegalovirus (CMV) immediate early gene promoter, the SV40 early promoter, and the Rous sarcoma virus long terminal repeat). In one embodiment, the promoter is a tissue specific promoter. Of particular interest are muscle specific promoters, and more particularly, cardiac specific promoters. These include the myosin light chain-2 promoter (Franz et al. (1994) *Cardioscience*, Vol. 5(4):235-43; Kelly et al. (1995) *J. Cell Biol.*, Vol. 129(2):383-396), the alpha actin promoter (Moss et al. (1996) *Biol. Chem.*, Vol. 271(49): 31688-31694), the troponin 1 promoter (Bhavsar et al. (1996) *Genomics*, Vol. 35(1):11-23); the Na+/Ca2+ exchanger promoter (Barnes et al. (1997) *J. Biol. Chem.*, Vol. 272(17): 11510-11517), the dystrophin promoter (Kimura et al. (1997) *Dev. Growth Differ.*, Vol. 39(3):257-265), the alpha7 integrin promoter (Ziober and Kramer (1996) *J. Bio. Chem., Vol.* 271(37):22915-22), the brain natriuretic peptide promoter (LaPointe et al. (1996) *Hypertension, Vol.* 27(3 Pt 2):715-22) and the alpha B-crystallin/small heat shock protein promoter (Gopal-Srivastava (1995) *J. Mol. Cell. Biol.*, Vol. 15(12): 7081-7090), alpha myosin heavy chain promoter (Yamauchi-Takihara et al. (1989) *Proc. Natl. Acad. Sci. USA*, Vol. 86(10): 3504-3508) and the ANF promoter (LaPointe et al. (1988) *J. Biol. Chem.*, Vol. 263(19):9075-9078).

In certain embodiments, the promoter operably linked to a polynucleotide encoding a miR-499 and/or a miR-208a/miR-208b inhibitor may be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR. An expression vector may encode a single nucleic acid that targets both miR-208 (e.g., miR-208a or miR-208b) and miR-499 as described herein, wherein the single nucleic acid is operably linked to a inducible promoter. Alternatively, a single expression vector may encode a miR-208a/miR-208b inhibitor and a miR-499 inhibitor, wherein the miR-208a/miR-208b inhibitor is driven by a first inducible promoter and the miR-499 inhibitor is driven by a second inducible promoter. In another embodiment, a first expression vector may encode a miR-208a/miR-208b inhibitor, wherein the miR-208a/miR-208b inhibitor is operably linked to a first inducible promoter and a second expression vector may encode a miR-499 inhibitor, wherein the miR-499 inhibitor is operably linked to a second inducible promoter. Other combinations of inducible and constitutive promoters for controlling the expression of the miR-208 (e.g., miR-208a or miR-208b) and miR-499 inhibitors are also contemplated. For instance, a miR-208a/miR-208b inhibitor may be expressed from a vector using a constitutive promoter, while a miR-499 inhibitor may be expressed from a vector using an inducible promoter.

The present invention also includes methods for scavenging or clearing miR-499 and miR-208a/miR-208b inhibitors following treatment. The method may comprise overexpressing binding sites for the miR-499 and miR-208a/miR-208b inhibitors in cardiac tissue. In another embodiment, the present invention provides a method for scavenging or clearing miR-499 and miR-208 (e.g., miR-208a or miR-208b) following treatment. In one embodiment, the method comprises overexpression of binding site regions for miR-499 and miR-208a/miR-208b in skeletal muscle using a skeletal and heart muscle specific promoter (muscle creatine kinase (MCK)). The binding site regions preferably contain a sequence of the seed region for miR-499 and miR-208a or miR-208b. The seed region is the 5' portion of a miRNA spanning bases 2-8, which is important for target recognition. In some embodiments, the binding site may contain a sequence from the 3'UTR of one or more targets of miR-499 or miR-208, such as THRAP1 or PURbeta. In another embodiment, a miR-499 and miR-208 inhibitor may be administered after miR-499 and miR-208 to attenuate or stop the function of the miRNA.

In another embodiment of the invention, the inhibitor of miR-208 (e.g., miR-208a or miR-208b) and the inhibitor of miR-499 are co-administered. The miR-208 inhibitor and miR-208 may be administered in a single formulation. For instance, a pharmaceutical composition comprising a miR-208 inhibitor and a miR-499 inhibitor can be used to co-administer the two inhibitors. Alternatively, the miR-208 and miR-499 inhibitors may be encoded by a single nucleic acid, such as an expression vector as described herein. Multiple co-administrations of the two inhibitors can be given over a sustained period of time, for instance, one week, two weeks, three weeks, one month, two months, three months, four months, five months, six months, nine months, one year, two years, three years, four years, or five years.

In some embodiments, the inhibitor of miR-208 (e.g., miR-208a or miR-208b) and the inhibitor of miR-499 are administered sequentially. In one embodiment, the inhibitor of miR-208 is administered prior to the inhibitor of miR-499. In another embodiment, the inhibitor of miR-499 is administered prior to the inhibitor of miR-208. The interval separating the administration of the miR-208 and miR-499 inhibitors may range from several minutes to several days. For instance, the interval can be about one hour to about 72 hours, six hours to about 48 hours, or about 12 hours to about 24 hours. In a preferred embodiment, the interval between the administration of the miR-208 inhibitor and the miR-499 inhibitor is at least 24 hours. The inventors have observed that administering a miR-499 inhibitor at least about 24 hours before a miR-208 inhibitor results in at least about a 50% reduction in stress-induced β-MHC expression at about three days after administration of the miR-208 inhibitor. In the absence of a miR-499 inhibitor, a comparable effect on stress-induced β-MHC expression is not observed until at least about two months after administration of the miR-208 inhibitor.

In other embodiments of the invention, more than one sequential administration of the miR-208 and miR-499 inhibitors may be employed to produce a sustained effect. In this regard, various combinations may be used. By way of illustration, where the inhibitor of miR-499 is "A" and the inhibitor of miR-208 (e.g., miR-208a or miR-208b) is "B", the following permutations based on 3 and 4 total administrations are exemplary:

| A/B/A   | B/A/B   | B/B/A   | A/A/B   | B/A/A   | A/B/B   |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B |         |         |

Other combinations are likewise contemplated.

Preferably, the expression or activity of miR-208 (e.g., miR-208a or miR-208b) and miR-499 is reduced in the heart cells of a subject following administration of the miR-208 inhibitor and the miR-499 inhibitor to the subject. In certain embodiments, the expression or activity of miR-208a/miR-208b and/or miR-499 is reduced by greater than 50%, greater than 60%, greater than 70%, greater than 75%, greater than 80%, greater than 85%, greater than 90%, or greater than 95% following administration of a miR-208 and miR-499 inhibitor. In one embodiment, the expression or activity of miR-208a/miR-208b and miR-499 is reduced by greater than 60 percent in the heart cells of the subject following administration of the inhibitors. In another embodiment, the expression or activity of miR-208a/miR-208b and miR-499 is reduced by greater than 80 percent in the heart cells of the subject following administration of the inhibitors. In still another embodiment, the expression or activity of miR-208a/miR-208b and miR-499 is reduced by greater than 90 percent in the heart cells of the subject following administration of the inhibitors.

The present invention also includes a method of regulating cardiac and/or skeletal muscle contractility. Adult skeletal muscle fibers can be categorized into fast and slow twitch subtypes based on specialized contractile and metabolic properties. These properties reflect the expression of specific sets of fast and slow contractile protein isoforms of myosin heavy and light chains, tropomyosin, and troponins, as well as myoglobin (Naya et al. (2000) *J Biol Chem*, Vol. 275(7): 4545-4548). Slow-twitch muscles are primarily used in chronic activities such as posture maintenance and sustained locomotor activity. Fast-twitch fibers are used primarily for high-force burst activities. The adult skeletal muscle phenotype is not static but instead retains the ability to adjust to variations in load bearing and contractile usage patterns, resulting in adaptations in morphology, phenotype, and contractile properties.

The up-regulation of several fast skeletal muscle contractile protein genes was observed in the hearts of mice lacking both miR-208a alleles. This up-regulation of fast skeletal muscle contractile protein genes in the hearts of miR-208a knockout mice indicates that miR-208 normally functions to repress the fast skeletal muscle gene program. A concomitant reduction of miR-499 expression was observed in miR-208a mutant mice (see Example 3), suggesting that miR-499 may also negatively regulate the expression of fast skeletal muscle contractile protein genes. As discussed above, miR-208b is also expressed predominantly in slow skeletal muscle (e.g., soleus). Thus, miR-208b may have profound effects on cardiac and skeletal muscle contractility in humans, and may also regulate the fast skeletal muscle gene program and determine fiber identity. The inventors have recently shown that miR-208b and miR-499 play important roles in the specification of muscle fiber identity by activating slow and repressing fast myofiber gene programs. The actions of these miRNAs are mediated in part by a collection of transcriptional repressors of slow myofiber genes, like Sox6, PURβ, Sp3 and HP1β. Using the skeletal muscle specific MCK-promoter miR-499 transgenic animals also revealed conversion to a slower myofiber type. Even more remarkably, when mice were subjected to a regimen of forced treadmill running, the miR-499 transgenic animals ran more than 50% longer than wild-type littermates, indicative of enhanced endurance resulting from the reprogramming of fast myofibers to a slower fiber type. See van Rooij et al. (2009) Developmental Cell, Vol. 17:662-673).

In one embodiment, the method of regulating cardiac and/or skeletal muscle contractility comprises administering a modulator of miR-499 and miR-208 (e.g., miR-208a or miR-208b) expression or activity to heart and/or skeletal muscle cells. In another embodiment, the method comprises administering a modulator of miR-499 and miR-208b. In another embodiment, there is provided a method of regulating cardiac contractile protein gene expression comprising administering a modulator of miR-499 and miR-208 (e.g., miR-208a or miR-208b) expression or activity to heart cells. In another embodiment, there is provided a method of regulating skeletal muscle contractile protein gene expression comprising administering to skeletal muscle cells a modulator of miR-499 and miR-208 (e.g., miR-208a or miR-208b) expression or activity. In another embodiment, there is provided a method of regulating skeletal muscle contractile protein gene expression comprising administering to skeletal muscle cells a modulator of miR-499 and miR-208b expression or activity. In still another embodiment, the present invention provides a method of inducing a fiber type switch of a skeletal muscle cell comprising administering to skeletal muscle cells a modulator of miR-499 and miR-208 expression or activity to the skeletal muscle cell. In another embodiment, the method of inducing a fiber type switch of a skeletal muscle cell comprises administering to skeletal muscle cells a modulator of miR-499 and miR-208b expression or activity. The modulator may be an agonist or an inhibitor of miR-499, miR-208, and/or miR-208b expression or activity. In some embodiments, the expression of THRAP1, PURbeta, myostatin, Sp3, HP 1β, and Sox 6 are increased in a cell by contacting the cell with a miR-499 and miR-208a (or miR-208b) inhibitor. In other embodiments, expression of THRAP1, PURbeta, myostatin, Sp3, HP 1β, and Sox 6 are decreased in a cell by contacting the cell with an agonist of miR-499 and miR-208a (or miR-208b).

In certain embodiments of the invention, there is provided a method of reducing β-MHC expression in heart cells comprising administering an inhibitor of miR-499 and miR-208 (e.g., miR-208a or miR-208b) expression or activity to the heart cells. In one embodiment, there is provided a method of reducing β-MHC expression in skeletal muscle cells comprising administering an inhibitor of miR-499 and miR-208b expression or activity to the skeletal muscle cells. In other embodiments of the invention, there is provided a method of elevating β-MHC expression in heart cells and/or skeletal muscle cells comprising increasing endogenous miR-499 and miR-208a (or miR-208b) expression or activity or administering exogenous miR-499 and miR-208a (or miR-208b) to heart cells and/or skeletal muscle cells.

In one embodiment of the invention, there is provided a method of increasing the expression of a fast skeletal muscle contractile protein gene in heart cells comprising administering to the heart cells an inhibitor of miR-499 and miR-208 (e.g., miR-208a or miR-208b) expression or activity. In another embodiment, there is provided a method of increasing the expression of a fast skeletal muscle contractile protein gene in skeletal muscle cells comprising administering to the skeletal muscle cells an inhibitor of miR-499 and miR-208b expression or activity. In another embodiment of the invention, there is provided a method of decreasing the expression of a fast skeletal muscle contractile protein gene in heart cells and/or skeletal muscle cells comprising increasing endogenous miR-499 and miR-208a (or miR-208b) expression or activity or administering exogenous miR-499 and miR-208a (or miR-208b) to the heart cells and/or skeletal muscle cells. Examples of fast skeletal muscle contractile protein genes that may be increased or decreased according to the methods of the present invention include, but are not limited to, troponin I2; troponin T3, fast skeletal myosin light chain, or alpha skeletal actin.

In skeletal muscle, the repression of slow fiber genes and activation of fast fiber genes is associated with numerous musculoskeletal disorders, including, but not limited to, disuse atrophy, muscle wasting in response to anti-gravity, and denervation. Thus, expression of miR-499 in combination with miR-208a or miR-208b in skeletal muscle cells may be useful in repressing fast fiber genes thereby activating the reciprocal expression of slow fiber genes. Accordingly, the present invention also encompasses a method for treating or preventing a musculoskeletal disorder in a subject in need thereof. In one embodiment, the method comprises administering an agonist of miR-208 (e.g., miR-208a or miR-208b) and an agonist of miR-499 to the subject, wherein the expression or activity of miR-208a/miR-208b and miR-499 is increased in the skeletal muscle cells of the subject following administration. In another embodiment, the method comprises administering an agonist of miR-208b and an agonist of miR-499 to the subject, wherein the expression or activity of miR-208b and miR-499 is increased in the skeletal muscle cells of the subject following administration. Preferably, the expression of one or more fast skeletal muscle genes in the skeletal muscle cells of the subject is reduced following administration of the miR-499 and miR-208a (or miR-208b) agonists. The one or more fast skeletal muscle genes can include, but is not limited to, troponin 12, troponin T3, fast skeletal myosin light chain, and alpha skeletal actin.

In another embodiment, the present invention provides a method of treating or preventing muscle wasting in response to a reduced gravity environment by administering an agonist of miR-499 and miR-208 (e.g., miR-208a or miR-208b) to the skeletal muscle. In another embodiment, the method of treating or preventing muscle wasting in response to a reduced gravity environment comprises administering an agonist of miR-499 and miR-208b to the skeletal muscle. In yet another embodiment, the present invention provides a method of treating or preventing muscle atrophy by administering an agonist of miR-499 and an agonist of miR-208 (e.g., miR-208a and/or miR-208b) to the skeletal muscle. In another embodiment, the method of treating or preventing muscle atrophy comprises administering an agonist of miR-499 and an agonist of miR-208b to the skeletal muscle.

In some embodiments, the agonist of miR-208 (miR208a or miR-208b) and the agonist of miR-499 are polynucleotides encoding a mature miR-208 (miR208a or miR-208b) and/or miR-499 sequence. In one embodiment, the polynucleotide comprises a mature miR-208a sequence (SEQ ID NO: 5) and a mature miR-499 sequence (SEQ ID NO: 14). In another embodiment, the polynucleotide comprises a mature miR-208b sequence (SEQ ID NO: 19) and a mature miR-499 sequence (SEQ ID NO: 14). In another embodiment, the agonist of miR-499 and agonist of miR-208 (miR208a or miR-208b) may be a polynucleotide comprising the pri-miRNA or pre-miRNA sequence for miR-499 and miR-208 (miR208a or miR-208b). Alternatively, the agonist of miR-208 (miR208a or miR-208b) and the agonist of miR-499 may be separate polynucleotides each comprising a mature sequence or pre-miRNA sequence of the miRNA. The polynucleotide comprising the mature miR-499 and/or miR-208 (miR208a or miR-208b) sequence may be single stranded or double stranded. The polynucleotides may contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-499, miR-208, and/or miR-208b sequence is conjugated to cholesterol.

In another embodiment, the agonist of miR-499 and miR-208 (miR208a or miR-208b) may be encoded on an expression vector. An expression vector for expressing miR-499 and miR-208 (miR208a or miR-208b) comprises at least one promoter operably linked to a polynucleotide encoding miR-499 and/or miR-208 (miR208a or miR-208b). The polynucleotide encoding miR-499 may encode the primary-miRNA-499 sequence (pri-miR-499), the precursor-miRNA-499 sequence (pre-miR-499) or the mature miR-499 sequence. The polynucleotide encoding miR-208a/miR-208b may encode the primary-miRNA-208a/208b sequence (pri-miR-208/pri-miR-208b), the precursor-miRNA-208/208b sequence (pre-miR-208a/pre-miR-208b) or the mature miR-208a/208b sequence. In some embodiments, the expression vector comprises a polynucleotide operably linked to a promoter, wherein said polynucleotide comprises the sequence of SEQ ID NO: 5 and SEQ ID NO: 14. In other embodiments, the expression vector comprises a polynucleotide operably linked to a promoter, wherein said polynucleotide comprises the sequence of SEQ ID NO: 19 and SEQ ID NO: 14. Such polynucleotides may be about 18 to about 2000 nucleotides in length, about 70 to about 200 nucleotides in length, about 20 to about 50 nucleotides in length, or about 18 to about 25 nucleotides in length. In another embodiment, the expression vector may express a miR-499 agonist (e.g. polynucleotide comprising a miR-499 sequence) and a miR-208 agonist (e.g. polynucleotide comprising a miR-208a or miR-208b sequence) from different promoters. Polynucleotides encoding miR-499, miR-208a, and/or miR-208b may be located in a nucleic acid encoding an intron or in a nucleic acid encoding an untranslated region of an mRNA or in a non-coding RNA.

In one embodiment, the expression vector may contain sequences from the $20^{th}$ intron from the Myh7b gene or sequences from the $31^{st}$ intron from the Myh7 (β-MHC) gene.

The agonist of miR-208a or miR-208b may be co-administered with the agonist of miR-499 to a subject. The two agonists may be administered in a single formulation, e.g. a pharmaceutical composition comprising a miR-208a or miR-208b agonist and a miR-499 agonist. Alternatively, the two agonists (e.g. miR-208a and miR-499 or miR-208b and miR-499) may be a single polynucleotide encoding the mature or pre-miRNA sequence of the two miRNAs. Multiple co-administrations of the two agonists can be given over a sustained period of time, for instance, one week, two weeks, three weeks, one month, two months, three months, four months, five months, six months, nine months, one year, two years, three years, four years, or five years.

In certain embodiments, the agonist of miR-208a or miR-208b and the agonist of miR-499 are administered sequentially. In one embodiment, the agonist of miR-208a or miR-208b is administered prior to the agonist of miR-499. In another embodiment, the agonist of miR-499 is administered prior to the agonist of miR-208a or miR-208b. The interval separating the administration of the agonists may range from several minutes to weeks, e.g. about one hour to about 72 hours, six hours to about 48 hours, or about 12 hours to about 24 hours. In a preferred embodiment, the interval between the administration of the miR-208a or miR-208b agonist and the miR-499 agonist is at least 24 hours.

The present invention also includes pharmaceutical compositions comprising an inhibitor or agonist of miR-499, miR-208a, and/or miR-208b. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of a miR-499 inhibitor and/or an effective dose of a miR-208a or miR-208b inhibitor. In another embodiment, the pharmaceutical composition comprises an effective dose of a miR-499 agonist and/or an effective dose of a miR-208a or miR-208b agonist. An "effective dose" is an amount sufficient to effect a beneficial or desired clinical result. An effective dose of an miRNA inhibitor or miRNA agonist of the invention may be about 1 mg/kg to about 200 mg/kg, about 20 mg/kg to about 160 mg/kg, or about 40 mg/kg to about 100 mg/kg. In one embodiment, the inhibitor of miR-208 or miR-208b and the inhibitor of miR-499 are administered each at a dosage of about 20 mg/kg to about 200 mg/kg. In another embodiment, the inhibitor of miR-208 or miR-208b and the inhibitor of miR-499 are administered each at a dosage of about 80 mg/kg. In another embodiment, the agonist of miR-208 or miR-208b and the agonist of miR-499 are administered each at a dosage of about 20 mg/kg to about 200 mg/kg. In still another embodiment, the agonist of miR-208 or miR-208b and the agonist of miR-499 are administered each at a dosage of about 80 mg/kg. The precise determination of what would be considered an effective dose may be based on factors individual to each patient, including their size, age, type of disorder (e.g. myocardial infarction, heart failure, cardiac hypertrophy, or musculoskeletal), and nature of inhibitor or agonist (e.g. antagomir, expression construct, antisense oligonucleotide, etc). Therefore, dosages can be readily ascertained by those of ordinary skill in the art from this disclosure and the knowledge in the art.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of miRNA function, polynucleotides encoding miRNA agonists, or constructs expressing particular miRNA inhibitors or agonists. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides or miRNA polynucleotide sequences (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising miRNA inhibitors, polynucleotides encoding miRNA sequence or expression constructs comprising miRNA sequences may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Any of the compositions described herein may be comprised in a kit. In one embodiment, the kit contains a first pharmaceutical composition comprising a miR-208a or miR-208b inhibitor and a second pharmaceutical composition comprising a miR-499 inhibitor. In another embodiment, the kit contains a single pharmaceutical composition comprising a miR-208a or miR-208b inhibitor and a miR-499 inhibitor. In another embodiment, the kit contains a first pharmaceutical composition comprising a miR-208a or miR-208b agonist and a second pharmaceutical composition comprising a miR-499 agonist. In still another embodiment, the kit contains a single pharmaceutical composition comprising a miR-208a or miR-208b agonist and a miR-499 agonist. In some embodiments, the kit may also include one or more transfection reagent(s) to facilitate delivery of the miRNA agonists or inhibitors to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed (e.g. sterile, pharmaceutically acceptable buffer and/or other diluents). However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

Such kits may also include components that preserve or maintain the miRNA agonist or miRNA inhibitors or that protect against their degradation. Such components may be DNAse-free, RNAse-free or protect against nucleases (e.g. RNAses and DNAses). Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering the miRNA agonist or inhibitor by various administration routes, such as parenteral or catheter administration.

It is contemplated that such reagents are embodiments of kits of the invention. Such kits, however, are not limited to the particular items identified above and may include any reagent used for the manipulation or characterization of miRNA.

The following examples are included solely to illustrate various aspects of the invention. The reference to miR208 in the Examples and figure refers to miR208a in mice. However, those of skill in the art should, in light of the present disclosure, appreciate that the invention is equally applicable to any human or other animal, and encompasses modulating either miR208a and/or miR208b.

EXAMPLES

Example 1

MiR-208 Knockout Mice Exhibit Reduced Cardiac Hypertrophy and Fibrosis in Response to Pressure Overload Encoded within an intron of the α-MHC gene is miR-208. Like α-MHC, miR-208 is expressed specifically in the heart with trace expression in the lung. miR-208 is processed out of the α-MHC pre-mRNA rather than being transcribed as a separate transcript. Intriguingly, however, miR-208 displays a remarkably long half-life of at least 14 days, and can thereby exert functions even when α-MHC mRNA expression has been down-regulated.

MiR-208 knockout mice were created by generating a miR-208 targeting vector by digesting a 0.4 kb fragment (5' arm) extending upstream of the miR-208 coding region with SacII and NotI and ligating the fragment into the pGKneoF2L2dta targeting plasmid upstream of the loxP sites and the Frt-flanked neomycin cassette. A 3.3 kb fragment (3' arm) was digested with SalI and HindIII and ligated into the vector between the neomycin resistance and Dta negative selection cassettes. Targeted ES-cells carrying the disrupted allele were identified by Southern blot analysis with 5' and 3' probes. Three miR-208 targeted ES clones were identified and used for blastocyst injection. The resulting chimeric mice were bred to C57BL/6 to obtain germline transmission of the mutant allele.

Although genetic deletion of miR-208 in mice failed to induce an overt phenotype, microarray analysis on hearts from wild-type and miR-208-/- animals at 2 months of age revealed removal of miR-208 to result in pronounced expression of numerous fast skeletal muscle contractile protein genes, which are normally not expressed in the heart. Thus, these results suggest that under normal conditions miR-208 is co-expressed with the sole cardiac-specific MHC gene to maintain cardiomyocyte identity by repressing the expression of skeletal muscle genes in the heart.

The most remarkable function of miR-208 was revealed by the aberrant response of miR-208 null mice to cardiac stress (van Rooij et al., (2007) Science, Vol. 316: 575-579). In response to pressure overload by thoracic aortic banding (TAB) that drives pathological remodeling of the heart, histological sections of hearts from miR-208 knockout mice showed virtually no hypertrophy of cardiomyocytes or fibrosis as compared to sections from wild-type mice (FIG. 1A). In addition, miR-208 knockout animals were unable to up-regulate β-MHC expression in response to pressure overload (FIGS. 1B and C). In contrast, other stress responsive genes, such as those encoding ANF and BNP, were strongly induced in miR-208 mutant animals (FIG. 1B), demonstrating that miR-208 is dedicated specifically to the control of β-MHC expression, which can be uncoupled from other facets of the cardiac stress response.

Example 2

Knockdown of miR-208 Phenocopies miR-208 Knockout Animals in Response to Stress

Figure 2:
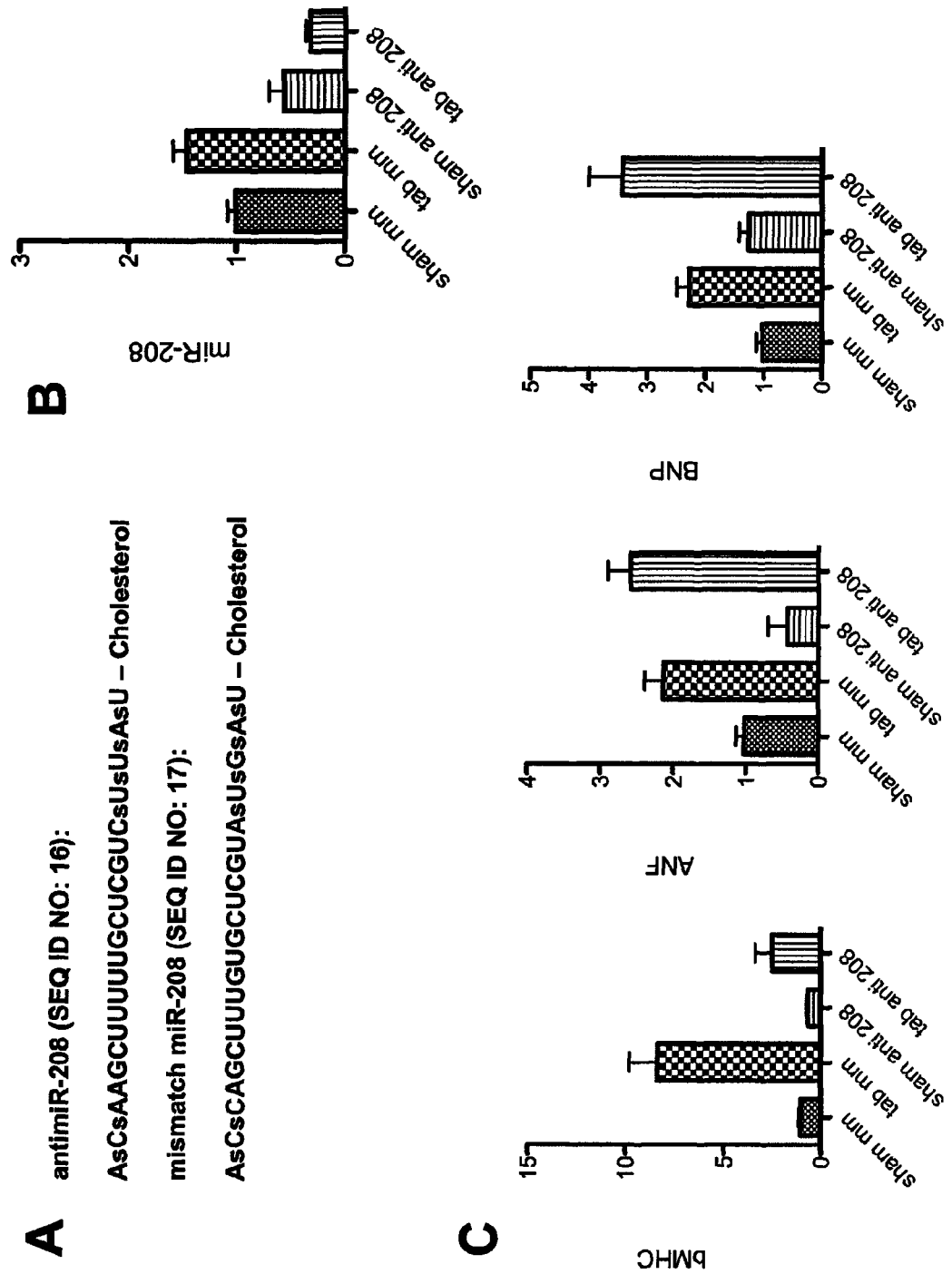
FIG. 2. Longterm knockdown of miR-208 phenocopies the inhibition of the stress response in the miR-208 knockout animals. A. Sequence of a synthetic oligonucleotide targeted to the mature miR-208 sequence (SEQ ID NO: 16). The mismatch control sequence contains four base mismatches compared to the anti miR-208 sequence (SEQ ID NO: 17). B. Realtime PCR analysis shows efficient knockdown of miR-208 in hearts of animals treated with the anti-miR-208 oligonucleotide. C. Relative expression levels for beta-myosin heavy chain (β-MHC), atrial natriuretic factor (ANF), and brain natriuretic peptide (BNP) in hearts of animals that received an anti-miR-208 oligonucleotide (anti 208) or a mismatched control (mm) after a sham or thoracic aortic banding (TAB) procedure. While the stress markers ANF and BNP are induced in response to TAB, the animals that received anti-miR-208 showed a decreased induction of βMHC expression.

To examine the specificity of the effect of the absence of miR-208 on the cardiac stress response, animals were injected intravenously daily with either an antagomir having a sequence complementary to the mature miR-208 sequence (anti 208; SEQ ID NO: 16) or a mismatched sequence (mm; SEQ ID NO: 17). All nucleosides were 2'-OMe modified, and the 5' terminal two and 3' terminal four bases contained a phosphorothioate internucleoside. Cholesterol was attached to the 3' end of the passenger strand through a hydroxyprolinol linker (FIG. 2A). Realtime PCR analysis of hearts of animals injected with the miR-208 antagomir two months after treatment showed efficient knockdown of miR-208 (FIG. 2B).

To test the effect of in vivo miR-208 downregulation on the cardiac stress response, animals receiving either the anti-miR-208 antagomir or the mismatched control were subject to a sham procedure or a thoracic aortic banding procedure to induce pressure overload. Animals that were treated with the mismatched control exhibited a typical stress response with upregulation of β-MHC as well as other stress genes (ANF and BNP). In contrast, animals that were treated with the anti-miR-208 antagomir failed to show an upregulation of β-MHC in response to the stress stimulus. However, an increase in expression of the other stress genes (ANF and BNP) was observed (FIG. 2C). The stress response of animals treated with the anti-miR-208 antagomir was remarkably similar to that of miR-208 knockout animals suggesting that miR-208 plays a critical role in the regulation of β-MHC expression in response to stress.

Example 3

MiR-208 is Required for Expression of miR-499

Figure 3:
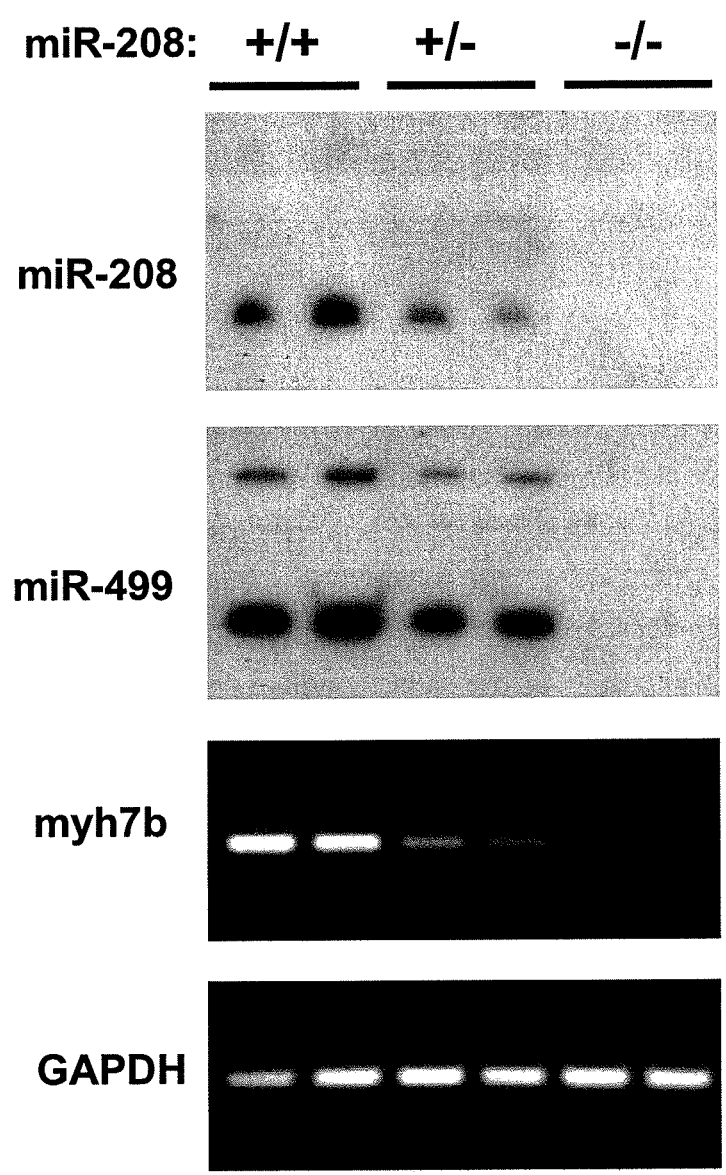
FIG. 3. Myh7b and miR-499 are regulated by miR-208. Northern blot showing expression of miR-499 in hearts of wild-type (+/+), miR-208 heterozygotes (+/−) and miR-208 knockout (−/−) mice. There is a direct correlation between the expression of miR-208 and miR-499, as well as Myh7b in wild-type and mutant mice. The expression of GAPDH was measured as a control.

To further explore the mechanism of action of miR-208 in the heart, the inventors defined the miRNA expression patterns in hearts from wild type and miR-208 knockout mice by microarray analysis. Among several miRNAs that were up- and down-regulated in miR-208 knockout hearts, the inventors discovered that miR-499 was highly abundant in normal hearts, but was not expressed above background levels in miR-208 knockout animals. These findings were confirmed by Northern blot (FIG. 3). Analysis of the genomic location of the miR-499 gene showed it to be contained within the 20$^{th}$ intron of the Myh7b gene, a homolog of the α-MHC gene. MiR-208 appears to regulate Myh7b and thereby miR-499 expression at the level of transcription since RT-PCR for Myh7b indicates that the mRNA of the host gene is dose-dependently abrogated in the absence of miR-208 (FIG. 3).

The Myh7b gene is conserved in vertebrates and is expressed solely in the heart and slow skeletal muscle (e.g. soleus) (FIG. 4A). Similarly, miR-499 has the same expression pattern as its host gene as confirmed by real-time PCR analysis (FIG. 4A & B). In situ hybridization using a probe directed against the 3' end of the Myh7b gene, indicated that this myosin (and miR-499) was expressed in heart as early as E10.5 (FIG. 4C). Later during embryogenesis, Myh7b/miR-499 is also expressed in the somites. These data indicate that miR-208 is required to drive an additional myosin, Myh7b, which gives rise to related miR-499. In addition, miR-499 is down-regulated during cardiac hypertrophy.

Figure 5:
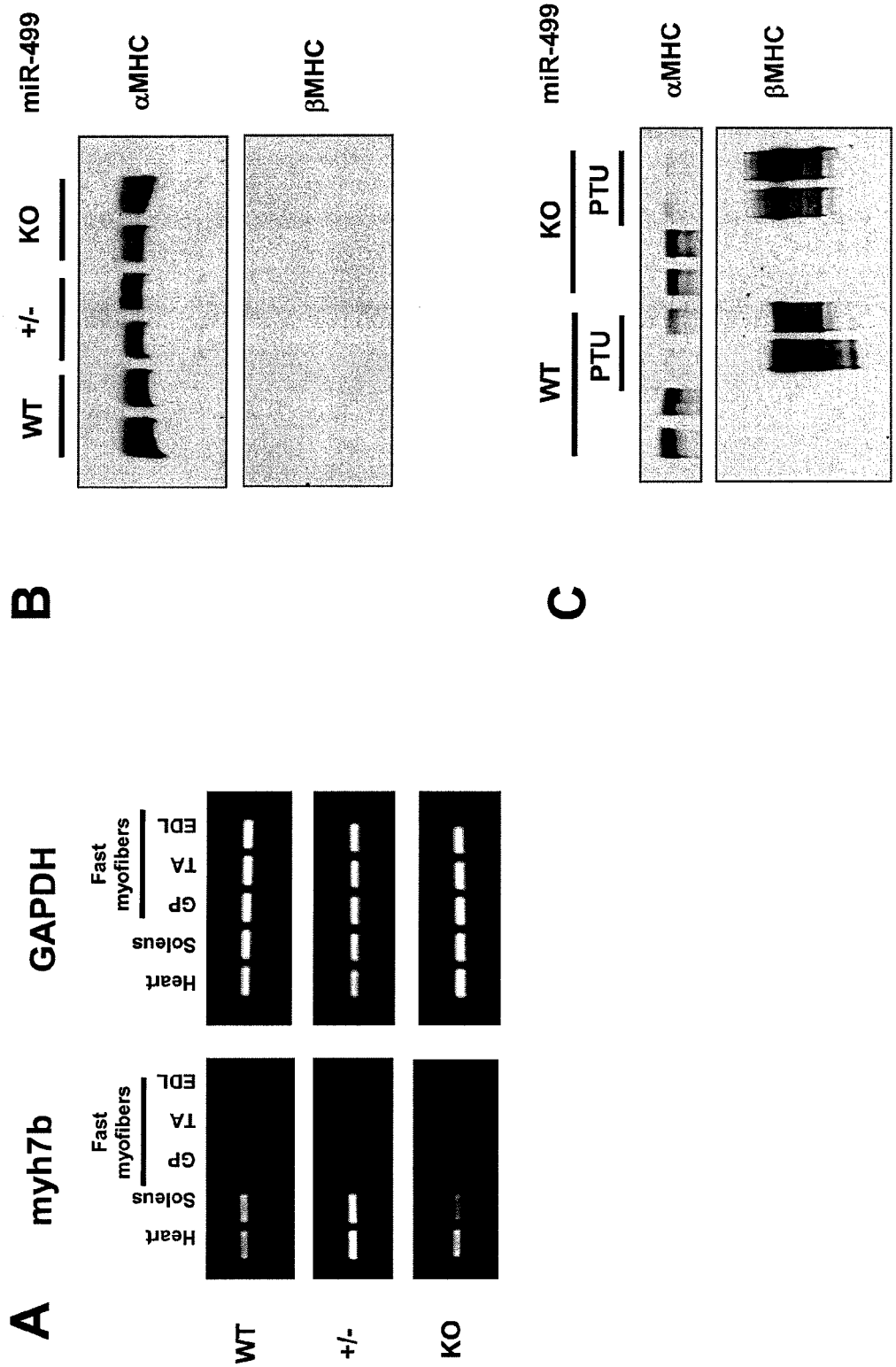
FIG. 5. MiR-499 does not affect myosin expression. A. RT-PCR analysis for Myh7b shows that genetic deletion of miR-499 does not affect the expression of its hostgene, Myh7b. GP-gastrocnemius/plantaris; TA-tibialis anterior; EDL-extensor digitorum longus. Expression of GAPDH was measured as a control. B. Western blot analysis of hearts from wild-type (WT), heterozygote (+/−), and miR-499 knockout (KO) animals for both α- and β-MHC shows that deletion of miR-499 does not affect the expression of either gene at the protein level. C. Propylthiouracil (PTU), which blocks thyroid hormone biogenesis and is a strong inducer of β-MHC, produces a decrease in α-MHC and an increase in β-MHC in both wildtype (WT) and miR-499 knockout (KO) animals.

To further explore the role of miR-499 in pathological cardiac hypertrophy and regulation of muscle contractility, miR-499 knockout animals were generated. Genetic deletion of miR-499 had no effect on expression of its host gene, Myh7b (FIG. 5A). Western blot analysis of hearts from miR-499 mutant and wild-type animals for both α- and β-MHC showed that deletion of miR-499 does not affect the expression of either gene at the protein level (FIG. 5B). To examine whether miR-499 had an effect on β-MHC regulation, wild-type and miR-499 knockout animals received propylthiouracil (PTU), which induces hypothyroidism and upregulates β-MHC. Both wild-type and miR-499 knockout animals exhibited a decrease in α-MHC and an increase in β-MHC in response to PTU (FIG. 5C). Surprisingly, unlike miR-208, miR-499 is not required for the regulation of expression of either α- or β-MHC.

Example 4

Dual Targeting of miR-208 and miR-499

MiR-208 regulates the expression of miR-499 as shown by the dose-dependent decrease in miR-499 expression in miR-208 heterozygote and miR-208 knockout animals (FIG. 3 and Example 3). To further elucidate the interaction between miR-208 and miR-499, wild-type animals were injected intravenously with saline or one of four doses (20 mg/kg, 40 mg/kg, 80 mg/kg, and 160 mg/kg) of a synthetic oligonucleotide (e.g. an antagomir) having a sequence complementary to the mature miR-208 sequence (anti-miR-208; SEQ ID NO: 16). Northern analysis of heart tissue three days after tail vein injection revealed a dose-dependent decrease in the expression of mature miR-208, while leaving the expression of the pre-miR-208 intact (FIG. 6A). However, unlike in the genetic deletion model, the expression of miR-499 remained unchanged. In addition, expression levels of β-MHC were also unaffected three days after injection of an anti-miR-208 antagomir (data not shown).

In a second series of experiments, wild-type animals were injected intravenously either with a single dose of anti-miR-208 (80 mg/kg), two sequential doses (80 mg/kg) of anti-miR-208 on two consecutive days, or two sequential doses (80 mg/kg) of a mismatched control oligonucleotide (SEQ ID NO: 17) on two consecutive days. Northern analysis of cardiac tissue two months after treatment showed that both miR-208 and miR-499 expression was reduced in animals treated with anti-miR-208 (FIG. 6B). Realtime PCR analysis confirmed these results (FIG. 6C). In addition, a decrease in expression of miR-208b, which is encoded within an intron of β-MHC and co-expressed with β-MHC, was also observed. Realtime PCR analysis for the corresponding host myosin genes revealed that knockdown of miR-208 does not affect the expression of α-MHC, but induces a decrease in the expression of β-MHC and Myh7b (FIG. 6C). A decrease in β-MHC protein was also observed two months after treatment with anti-miR-208 (FIG. 6D). These results indicate miR-208 regulation of miR-499 and β-MHC expression occurs after a delay suggesting that miR-208 is upstream of miR-499, which in turn is upstream of β-MHC. Thus, both miR-208 and miR-499 need to be downregulated to obtain an expedited reduction of β-MHC expression. MiR-208 downregulation alone leads to an eventual decrease in miR-499 expression, which in turn induces a decrease in β-MHC expression. To obtain a more immediate effect on β-MHC expression, both miR-499 and miR-208 can be targeted for downregulation.

Figure 7A:
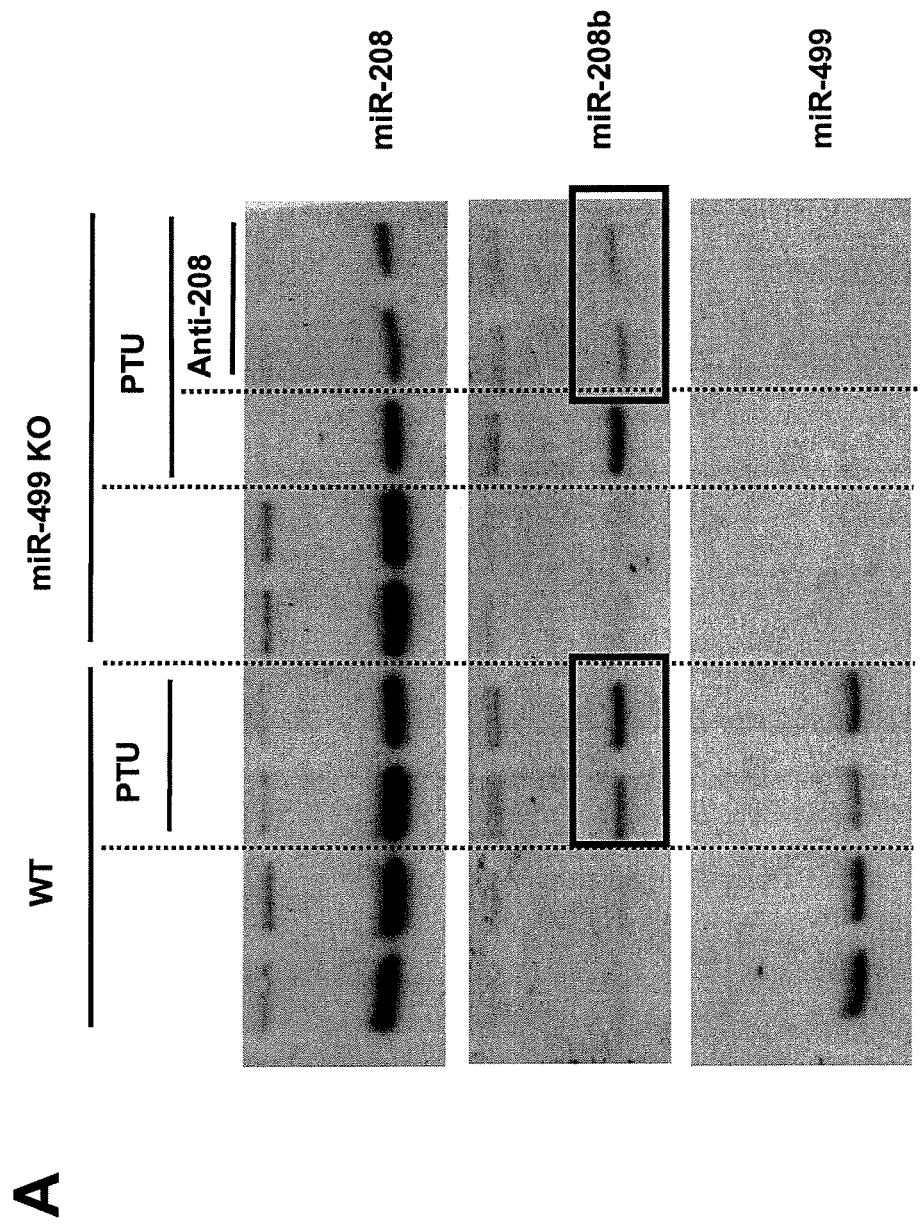
FIG. 7. Dual Targeting of miR-208 and miR-499. A. Northern analysis for miR-208, miR-208b and miR-499 in cardiac tissue of wild-type and miR-499 knockout animals shows a strong induction of miR-208b in response to PTU. MiR-208b is co-expressed with β-MHC and is indicative of its expression. In the miR-499 knockout animals, the induction of miR-208b is comparable to wild-type. However, knockdown of miR-208 in miR-499 knockout animals suppresses the induction of miR-208b expression by PTU. B. Realtime PCR analysis for miR-208, α-MHC, and β-MHC in cardiac tissue of wild-type animals, miR-208 knockout animals, miR-499 knockout animals, and miR-499 knockout animals treated with anti-miR-208 in the presence and absence of PTU.
Figure 7B:
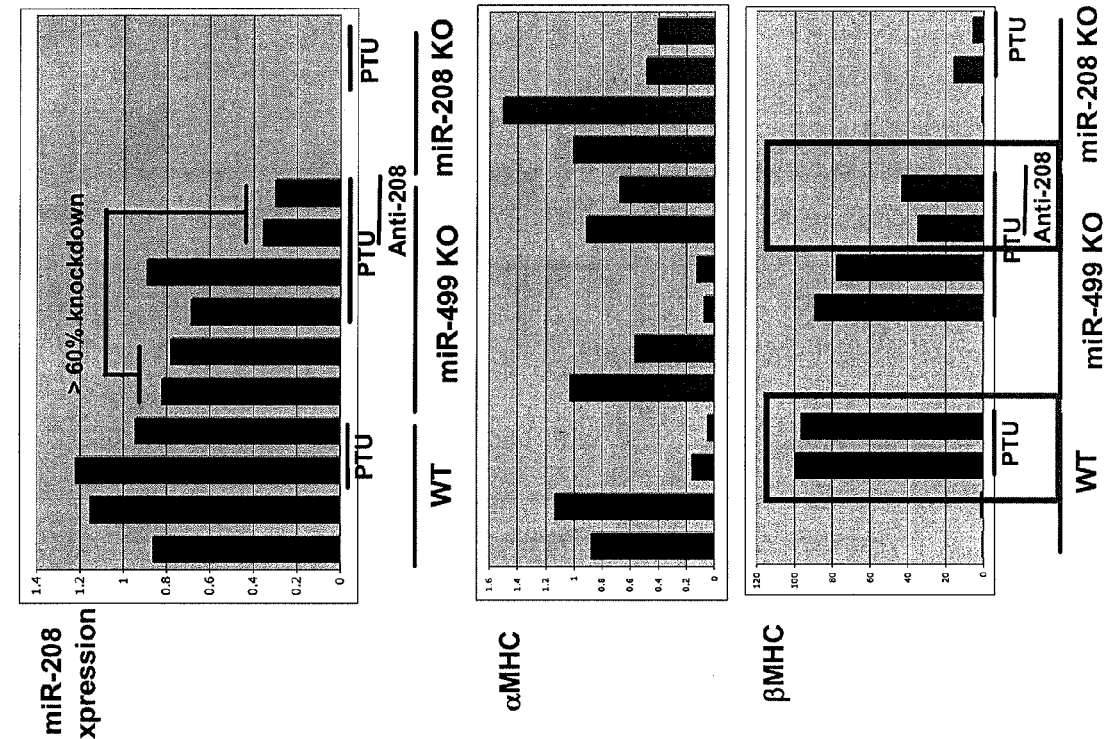

To examine the combined effect of downregulating both miR-208 and miR-499, miR-499 knockout animals were administered anti-miR-208 oligonucleotides prior to receiving propylthiouracil (PTU), an inducer of β-MHC expression. Similar to previous results, PTU induced a decrease in α-MHC expression and an increase in β-MHC/miR-208b expression (miR-208b is co-expressed with β-MHC) in both wild-type and miR-499 knockout animals in the absence of treatment with anti-miR-208 oligonucleotides (FIG. 7A, B). Such effects are characteristic of the cardiac stress response. In contrast, northern and realtime PCR analysis of cardiac tissue from miR-499 knockout animals treated with anti-miR-208 oligonucleotides two weeks after treatment showed that an increase in β-MHC/miR-208b expression in response to PTU was not observed (FIG. 7A,B). The response of the miR-499 knockout animals treated with anti-miR-208 resembled the response of miR-208 knockout animals (FIG. 7B). These results suggest that efficient and rapid downregulation of β-MHC can be achieved by targeting both miR-208 and miR-499. The dosage of anti-miR-208 oligonucleotides that were administered to the animals produced a 60% reduction in miR-208 expression. This percentage reduction was sufficient to suppress the induction of β-MHC by PTU in the absence of miR-499 (FIG. 7B). These findings indicate that reduction of both miR-499 and miR-208 may be an efficient therapeutic strategy for the treatment of cardiac disorders, such as pathological cardiac hypertrophy and heart failure.

Example 5

Knockdown of miR-208 and miR-499 Inhibits the Cardiac Stress Response

To further assess the therapeutic value of targeting miR-208 and miR-499 for treating cardiac disorders, mice are injected intravenously with an antisense oligonucleotide having a sequence complementary to the mature miR-208a sequence (anti-208), an antisense oligonucleotide having a sequence complementary to the mature miR-499 sequence (anti-499), or both anti-208 and anti-499 oligonucleotide sequences. Both anti-208 and anti-499 contain a combination of locked nucleic acids (LNA) and deoxyribonucleic acids (DNA) linked by phosphorothioate internucleoside linkages. Realtime PCR analysis of hearts of animals injected with the antisense oligonucleotides three weeks up to two months after treatment is used to assess knockdown of miR-208 and miR-499.

To test the effect of in vivo miR-208 and miR-499 downregulation on the cardiac stress response, animals receiving the anti-208, anti-499, or both the anti-208 and anti-499 oligos are subject to a sham procedure or a thoracic aortic banding procedure to induce pressure overload. Animals that are untreated are expected to exhibit a typical stress response with upregulation of β-MHC as well as other stress genes (ANF and BNP). In contrast, animals that are treated with both anti-208 and anti-499 are expected to exhibit a reduced upregulation of β-MHC in response to the stress stimulus that is more pronounced than animals receiving either antisense oligo alone.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of reducing a cardiac stress response in a subject in need thereof comprising administering to the subject:

an inhibitor of miR-208a or miR-208b, wherein the inhibitor of miR-208a or miR-208b is an antisense oligonucleotide comprising a sequence that is sufficiently complementary to a miR-208a or miR-208b sequence to hybridize to the miR-208a or miR-208b sequence under physiological conditions and inhibit the expression or activity of miR-208a or miR-208b in heart cells of said subject; and an inhibitor of miR-499, wherein the inhibitor of miR-499 is an antisense oligonucleotide comprising a sequence that is sufficiently complementary to a miR-499 sequence to hybridize to the miR-499 sequence under physiological conditions and inhibit the expression or activity of miR-499 in heart cells of said subject, and wherein the cardiac stress response is reduced in the subject within two weeks of administration of the inhibitors.

2. The method of claim 1, wherein the inhibitor of miR-208a or miR-208b and the inhibitor of miR-499 are co-administered.

3. The method of claim 2, wherein the inhibitor of miR-208a or miR-208b and the inhibitor of miR-499 are encoded by an expression vector.

4. The method of claim 3, wherein the inhibitor of miR-208a or miR-208b and the inhibitor of miR-499 are encoded by the same expression vector.

5. The method of claim 1, wherein the inhibitor of miR-208a or miR-208b and the inhibitor of miR-499 are administered sequentially.

6. The method of claim 5, wherein the inhibitor of miR-208a or miR-208b is administered prior to the inhibitor of miR-499.

7. The method of claim 5, wherein the inhibitor of miR-499 is administered prior to the inhibitor of miR-208a or miR-208b.

8. The method of claim 5, wherein the inhibitor of miR-208a or miR-208b and the inhibitor of miR-499 are administered at least 24 hours apart.

9. The method of claim 1, wherein the inhibitor of miR-208a or miR-208b and the inhibitor of miR-499 are administered at a dosage of about 1 mg/kg to about 200 mg/kg.

10. The method of claim 1, wherein the expression or activity of miR-208a or miR-208b and miR-499 is reduced by greater than 60 percent in the heart cells of the subject following administration of the inhibitors.

11. The method of claim 1, wherein the cardiac stress response includes cardiomyocyte hypertrophy, fibrosis of the heart, reduced expression of α-MHC in the heart cells, and/or increased expression of β-MHC in the heart cells of said subject.

12. The method of claim 1, wherein the inhibitor of miR-208a or miR-208b is an antisense oligonucleotide comprising a sequence that is at least 85% complementary to SEQ ID NO: 5 or SEQ ID NO: 19.

13. The method of claim 1, wherein the inhibitor of miR-208a or miR-208b is an antisense oligonucleotide comprising a sequence that is at least 95% complementary to SEQ ID NO: 5 or SEQ ID NO: 19.

14. The method of claim 1, wherein the inhibitor of miR-208a or miR-208b is an antisense oligonucleotide comprising a sequence that is 100% complementary to SEQ ID NO: 5 or SEQ ID NO: 19.

15. The method of claim 1, wherein the inhibitor of miR-499 is an antisense oligonucleotide comprising a sequence that is at least 85% complementary to SEQ ID NO: 14.

16. The method of claim 1, wherein the inhibitor of miR-499 is an antisense oligonucleotide comprising a sequence that is at least 95% complementary to SEQ ID NO: 14.

17. The method of claim 1, wherein the inhibitor of miR-499 is an antisense oligonucleotide comprising a sequence that is 100% complementary to SEQ ID NO: 14.

18. The method of claim 1, wherein the miR-208a or miR-208b antisense oligonucleotide and the miR-499 antisense oligonucleotide comprise at least one sugar and/or backbone modification.

19. The method of claim 18, wherein said at least one sugar modification is a bicyclic sugar nucleoside modification, 2'-O-alkyl modification, or 2'-fluoro modification.

20. The method of claim 19, wherein said bicyclic sugar nucleoside modification is a locked nucleic acid.

21. The method of claim 18, wherein said at least one backbone modification is a phosphorothioate linkage.

22. The method of claim 1, wherein the miR-208a or miR-208b antisense oligonucleotide and the miR-499 antisense oligonucleotide are about 8 to about 18 nucleotides in length.

23. The method of claim 1, wherein the miR-208a or miR-208b antisense oligonucleotide and the miR-499 antisense oligonucleotide are about 12 to about 16 nucleotides in length.

24. The method of claim 1, wherein the inhibitor of miR-208a or miR-208b and the inhibitor of miR-499 are present in separate compositions.

25. The method of claim 1, wherein the inhibitor of miR-208a or miR-208b and the inhibitor of miR-499 are present in the same composition.

26. The method of claim 1, wherein the subject is at risk for developing pathologic cardiac hypertrophy, heart failure, or myocardial infarction.

* * * * *

UNITED STATES PATENT AND TRADEMARK OFFICE
CERTIFICATE OF CORRECTION

PATENT NO. : 8,629,119 B2
APPLICATION NO. : 13/147784
DATED : January 14, 2014
INVENTOR(S) : Olson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

Signed and Sealed this
Thirtieth Day of May, 2017

Michelle K. Lee
*Director of the United States Patent and Trademark Office*